(12) United States Patent
Porter et al.

(10) Patent No.: US 11,766,558 B2
(45) Date of Patent: Sep. 26, 2023

(54) BIOMEDICAL ELECTRODE WITH ANTI-MICROBIAL PROPERTIES

(71) Applicant: Compass Health Brands Corp., Middleburg Heights, OH (US)

(72) Inventors: Justin Porter, Chattanooga, TN (US); Gary Chad Morgan, Chattanooga, TN (US); Anthony Shaw, Chattanooga, TN (US); Jenifer Adams, Fenton, MO (US)

(73) Assignee: Compass Health Brands Corp., Middleburg Heights, OH (US)

( * ) Notice: Subject to any disclaimer, the term of this patent is extended or adjusted under 35 U.S.C. 154(b) by 622 days.

(21) Appl. No.: 16/380,995

(22) Filed: Apr. 10, 2019

(65) Prior Publication Data

US 2020/0030597 A1 Jan. 30, 2020

Related U.S. Application Data

(60) Provisional application No. 62/711,680, filed on Jul. 30, 2018.

(51) Int. Cl.
| | | |
|---|---|---|
| *A61N 1/04* | (2006.01) | |
| *A61K 9/06* | (2006.01) | |
| *A61K 33/22* | (2006.01) | |

(52) U.S. Cl.
CPC .............. *A61N 1/0496* (2013.01); *A61K 9/06* (2013.01); *A61K 33/22* (2013.01); *A61N 1/0456* (2013.01);
(Continued)

(58) Field of Classification Search
CPC .. A61N 1/0492; A61N 1/0456; A61N 1/0496; A61H 2201/10; A61K 9/06;
(Continued)

(56) References Cited

U.S. PATENT DOCUMENTS

| | | | | |
|---|---|---|---|---|
| 4,539,996 A | * | 9/1985 | Engel ................... | A61N 1/0456 600/392 |
| 6,356,779 B1 | * | 3/2002 | Katzenmaier .......... | A61N 1/046 600/391 |

(Continued)

FOREIGN PATENT DOCUMENTS

| | | |
|---|---|---|
| CN | 108209907 A | 6/2018 |
| WO | 2000007603 A2 | 2/2000 |
| WO | 2020028358 A1 | 2/2020 |

OTHER PUBLICATIONS

"International Search Report and Written Opinion for PCT Patent Application No. PCT/US2019/044125", dated Nov. 14, 2019, 7 pages.

*Primary Examiner* — Carl H Layno
*Assistant Examiner* — Anh-Khoa N Dinh
(74) *Attorney, Agent, or Firm* — Cooper & Maersch LLC; Lorri W. Cooper

(57) ABSTRACT

A biomedical electrode for electrically contacting a user's skin includes a carrier layer, a backing layer, an electrical lead, a conductive member, and a gel contact member. The backing layer is disposed on the carrier layer. The electrical lead is positioned at least in part below the carrier layer. The conductive member is coupled to the electrical lead. The gel contact member is electrically coupled to the conductive member for directly contacting the user's skin. The gel contact member is electrically conductive. The gel contact member includes a gel combined with an anti-microbial agent.

6 Claims, 5 Drawing Sheets

(52) U.S. Cl.
CPC ........ *A61N 1/0492* (2013.01); *A61H 2201/10* (2013.01)

(58) Field of Classification Search
CPC ..... A61K 33/22; A61L 15/58; A61L 24/0015; A61L 24/0031; A61L 24/046; A61L 26/0019; A61L 26/008; A61L 15/44; A61L 2300/404; A61P 31/04; A61P 31/12; A61P 17/02
See application file for complete search history.

(56) References Cited

U.S. PATENT DOCUMENTS

| | | |
|---|---|---|
| 7,255,874 B1 | 8/2007 | Bobo et al. |
| 7,477,938 B2 | 1/2009 | Sun et al. |
| 7,477,940 B2 | 1/2009 | Sun et al. |
| 7,480,530 B2 | 1/2009 | Sun et al. |
| 7,486,989 B2 | 2/2009 | Sun et al. |
| 7,939,570 B2 | 5/2011 | Raul et al. |
| 8,239,017 B2 | 8/2012 | Sun et al. |
| 8,280,481 B2 | 10/2012 | Copp et al. |
| 8,632,838 B2 | 1/2014 | Roth et al. |
| 8,744,567 B2 | 6/2014 | Fassih et al. |
| 8,877,882 B1 | 11/2014 | Salamone et al. |
| 9,050,452 B2 | 6/2015 | Sun et al. |
| 9,278,155 B2 | 3/2016 | Asmus et al. |
| 9,550,053 B2 | 1/2017 | Ross |
| 9,764,069 B2 | 9/2017 | Roth et al. |
| 2003/0163185 A1* | 8/2003 | Carson .................... A61N 1/046 607/142 |
| 2004/0249432 A1* | 12/2004 | Cohen .................. A61N 1/0452 607/149 |
| 2005/0004550 A1 | 1/2005 | Sun et al. |
| 2005/0010192 A1* | 1/2005 | Sun .......................... A61N 1/30 604/501 |
| 2005/0177092 A1 | 8/2005 | Adachi et al. |
| 2005/0244484 A1* | 11/2005 | Flick .................... A61N 1/0468 424/445 |
| 2006/0127462 A1* | 6/2006 | Canada ................ D06M 15/564 442/128 |
| 2011/0111029 A1 | 5/2011 | Schmitz et al. |
| 2013/0325096 A1 | 12/2013 | Dupelle et al. |
| 2017/0095431 A1 | 4/2017 | Andrews et al. |
| 2017/0100585 A1 | 4/2017 | Hall et al. |
| 2018/0147155 A1 | 5/2018 | Yamabe et al. |

* cited by examiner

BIOMEDICAL ELECTRODE WITH ANTI-MICROBIAL PROPERTIES

CROSS-REFERENCE TO RELATED APPLICATION

This application claims priority to U.S. Provisional Application No. 62/711,680, filed on Jul. 30, 2018, the disclosure of which is incorporated herein by reference in its entirety.

FIELD

The invention relates to a biomedical electrode having antimicrobial properties and a method of manufacturing a biomedical electrode.

BACKGROUND

An electrode for biomedical applications, such as transcutaneous electrical nerve stimulation (TENS), is known. Biomedical electrodes include a connection for attaching to an external device and a pad that attaches to the skin of a user. The electrode pad typically has an adhesive layer that adheres to the user's skin. One type of adhesive layer is a gel layer. Proper operation of an electrode requires good electrical contact to the skin during usage.

Electrode terminals are an electrically conductive element or member to which electrical voltages and/or currents are supplied by an external TENS unit. The electrode terminal is typically disposed on an upper surface of the electrode and is not in direct contact with the skin. There are two common types of electrode connections or terminals. One is a snap connector (not shown) and the other is a pigtail connector 36. Pigtail connectors 36 are the most widely used fitting for TENS devices. These electrodes have a short wire extending from the electrode that is used as the connection point to electrical leads from the TENS device. They are generally easy to attach to the leads from the TENS device. Connector pins are usually specified at 2 mm, but have a generally accepted variance of from 1.8 mm to 2.2 mm.

Snap connectors have a standard 3.5 mm diameter snap fitting positioned on the top surface of the electrode. Lead wires from the TENS unit couple to the electrode through the snap fitting. The snap fitting offers a strong attachment point to ensure the electrode stays in place and remains connected to the TENS machine while in use.

Electrodes have a contact member in the nature of an electrode pad, which is the portion of the electrode that contacts the skin of a user. The electrode pad is designed to make a good and long-term electrical contact to the skin of the user while at the same time having good electrical contact to the electrode terminal. The electrode pad is typically electrically conductive and soft or flexible to allow for a tight alignment to the surface of the user's skin. The electrode pad may be larger than the electrode terminal to ensure that the terminal is completely covered and cannot directly contact the user's skin.

Electrode pads are a required part of an electrode to have proper skin contact during periods of electrical stimulation. To enhance skin contact and comfort, carbon, silver or silver chloride electrodes may be used in combination with liquid or solid hydrogel as a medium between the skin and electrode.

Electrodes can contain a cloth outer later and a self-adhering gel for applying to the skin. One type of cloth than can be used is a non-woven material, which can render the pad flexible and breathable. Other types of cloth may also be used. One type of gel that may be used for the electrode pad is hydrogel. Electrode pads containing a hydrogel are easy to apply and remove. The hydrogel has adhesive properties that allows the pad to stick to the skin but be easily removed and replaced for multiple applications. Hydrogels are beneficial because they distribute the current from the TENS device well.

Electrodes also typically include a conductive layer, which could be a carbon material or conductive ink, among other conductive materials. One type of carbon material is a carbon-filled polymeric film, with or without the addition of a silver coating. Electrodes can also include a foam backing. Electrodes come in a range of shapes and sizes. Some common shapes and sizes include square, round, oval, hand-shaped, gourd-shaped, butterfly, and strips. Reusable pads can last anywhere from 10 to 20 uses and their lifespan can be improved with appropriate care and storage.

SUMMARY

An antimicrobial biomedical electrode having bacteriostatic and/or bactericidal properties is shown and described.

DETAILED DESCRIPTION

Figure 1:
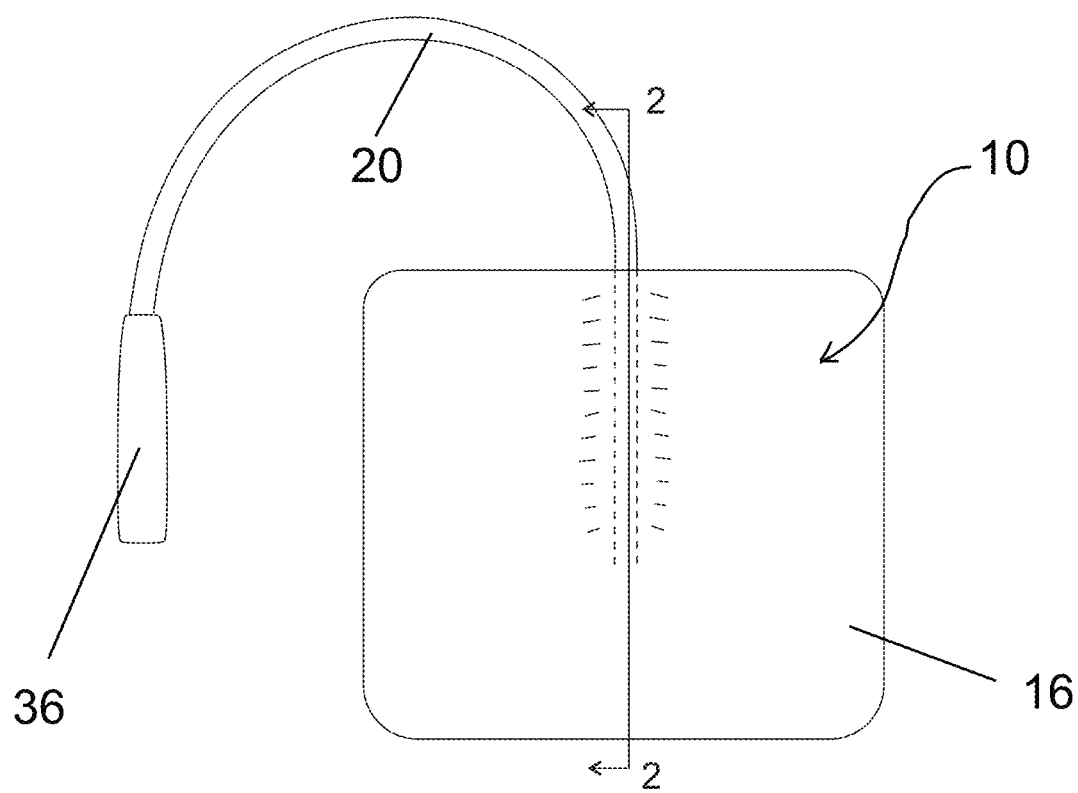
FIG. 1 depicts a top view of a first electrode according to an embodiment of the invention.

The embodiments discussed herein are discussed in the context of transcutaneous electrical nerve stimulation (TENS). TENS is primarily used on humans but is applicable to all mammals. It should be noted that the approach discussed herein is equally applicable to many other areas that utilize electrodes 10, including functional electrical stimulation (FES), electrocardiography (ECG), electroencephalography (EEG) or electrical impedance tomography (EIT), among others.

TENS is the use of electric current produced by a device to stimulate nerves for therapeutic purposes. One main application of TENS devices is pain relief. In one type of TENS, the electrical signal is applied to the skin using a pair of electrodes 10. Stimulation can be performed using one electrode 10 or more than one electrode 10 at the same time, such as on electrodes positioned on different areas of a user's body. Stimulation can also be focused on a principal area of a person's body in an area of acute pain.

Electrode pads 12 may absorb a user's sweat, which can lead to the electrode pad 12, and thus the electrode 10, being spoiled by bacteria or microbes from the user's skin. In addition, electrodes 10 are often used in locations that are prone to bacteria and microbes, such as in doctor's offices, gyms, spas, and the like.

The electrodes 10 described herein are advantageous to the user in that they have anti-microbial properties that deter the electrode pads 12 from being spoiled due to contact with the user's skin or due to outside contamination. The inventive electrodes 10 deliver antimicrobial properties to the skin and provide a zone of inhibition 14 under and around the electrode 10 site that is greater in dimension than the actual size/perimeter of the electrode 10. The treatment of the pads 12 with an anti-microbial agent helps to retain the life of the electrode pads 12 and helps to protect a user's skin so that the user is not exposed to skin conditions and rashes associated with spoiled electrode pads 12. The anti-microbial treatment of the electrode pads 12 helps to prolong the life of the pads 12 and keeps them safe throughout useful life. In addition, because the electrode pads 12 are made bacteriostatic and/or bactericidal, they are better suited for clinical applications where the electrode pads 12 may be subjected to contamination from the clinical setting.

The electrode pads 12 of the present invention incorporate advantages of present-day electrodes 10, including the use of hydrogels and flexibility associated with today's pads, while, at the same time incorporating an antimicrobial.

The electrode 10 includes an array of layers that includes a top layer 16 that extends away from user's skin and a bottom layer (or pad) 12 that attaches to the user's skin. In building the electrode 10 array, the electrode 10 includes:

1) A top layer 16 is an insulator cloth, a foam layer, or a combination of cloth and foam. In a preferred embodiment, the top layer 16 is cloth. The foam may be occlusive or non-occlusive. The top layer 16 may also be vinyl or other materials.

2) An insulator layer 18 may be coupled below the top layer 16 to assist with pull strength, to prevent delamination, and to protect against potato-chipping of the top layer. This layer 18 may be made of a Mylar material, among other materials.

3) An electrical lead wire 20 and an associated layer 22 for holding the lead wire in place are positioned below the top layer 16. The layer 22 for holding the lead wire 20 in place may be an adhesive.

4) A conductive layer 24, which may be a carbon film, is positioned below the electrical lead wire 20 and associated holding layer 22. The conductive carbon film 24 is coupled electrically to the electrical lead wire 20. The conductive layer 24 may alternatively be other conductive materials.

5) A silver coating layer 26 (shown in FIG. 3) may optionally be positioned below the conductive carbon film 24 and is utilized to increase the conductivity of the conductive carbon film 24.

6) A bottom layer 12 is a gel layer that is positioned below the conductive 24 and/or silver coating 26 layer (when provided). The gel layer 12 attaches directly to a user's skin. The gel layer 12 is conductive and provides an interface between the conductive layer 24 and the subject's skin to deliver current to and receive signals from the subject's body. The gel layer 12 can cover more than the complete bottom surface of conductive element 24. For example, the conductive gel layer 12 can extend at least ¼ inch beyond the edges (e.g. footprint) of conductive element 24, if desired. Alternatively, the gel layer 12 may be the same size and shape as the other layers of the electrode 10, as shown in FIG. 2.

The gel layer 12 serves as a buffering agent to insulate the user from the electrical current of the lead wire 20. The gel layer 12 may comprise a combination of several layers positioned one on top of the other, with an adhesive layer 32 provided between the gel layers 12. The lowermost gel layer 12b, e.g., the layer that attaches to a user's skin, includes as a component Benzethonium Chloride (commonly referred to by the acronym "BEC"), which is an anti-microbial agent that provides bacteriostatic and bactericidal properties.

Benzethonium chloride is a synthetic quaternary ammonium salt that is typically an odorless, white solid that is soluble in water. The US Food and Drug Administration specifies that the safe and effective concentrations for BEC are 0.1-0.2% weight per volume (e.g., density, such as grams/liter or mg/ml)) in first aid products. (See Tentative Final Monograph (21 CFR 222), May 22, 2014). Aqueous solutions of BEC are not known to be absorbed through the skin. BEC is also found in commercial grapefruit seed extract preparations.

Figure 2:
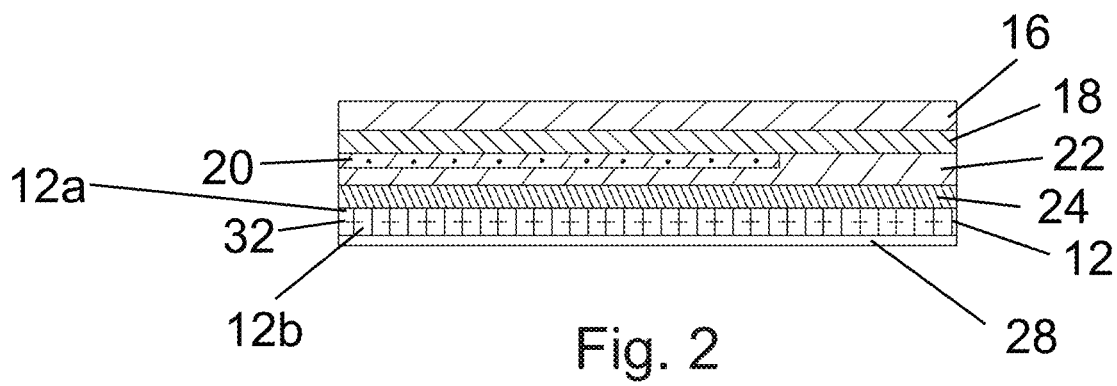
FIG. 2 shows a section through the first electrode along line 2-2 of FIG. 1.

Referring to FIG. 2, the uppermost layer 12a of the gel layer 12 may only be formed from gel or could be a combination of gel and another material, such as a different anti-microbial or other materials. The antimicrobial component is mixed in with the gel material of the hydrogel layer 12b so that the antimicrobial becomes integrated into the gel layer 12. Alternatively, a single gel layer 12 can be provided with the entire layer including a mixture with the antimicrobial. The antimicrobial could be applied in a layer as an alternative, or as a mixture with another material as a layer.

7) A removable backing layer 28, such as a polyethylene film, is applied to the gel layer 12 and is removed prior to application of the electrode 10 to a user's skin. Because the electrode 10 is reusable, the backing layer 28 is saved and reused after the user has completed use of the electrode 10.

Another layer used in the manufacture of the electrode 10 is a sacrificial liner, which is provided to allow the lead wire 20 to be inserted into the electrode 10. This layer is not positioned in the electrode 10 after manufacture but is used to assist in the manufacturing of the electrode 10 to install the lead wire 20.

Figure 3:
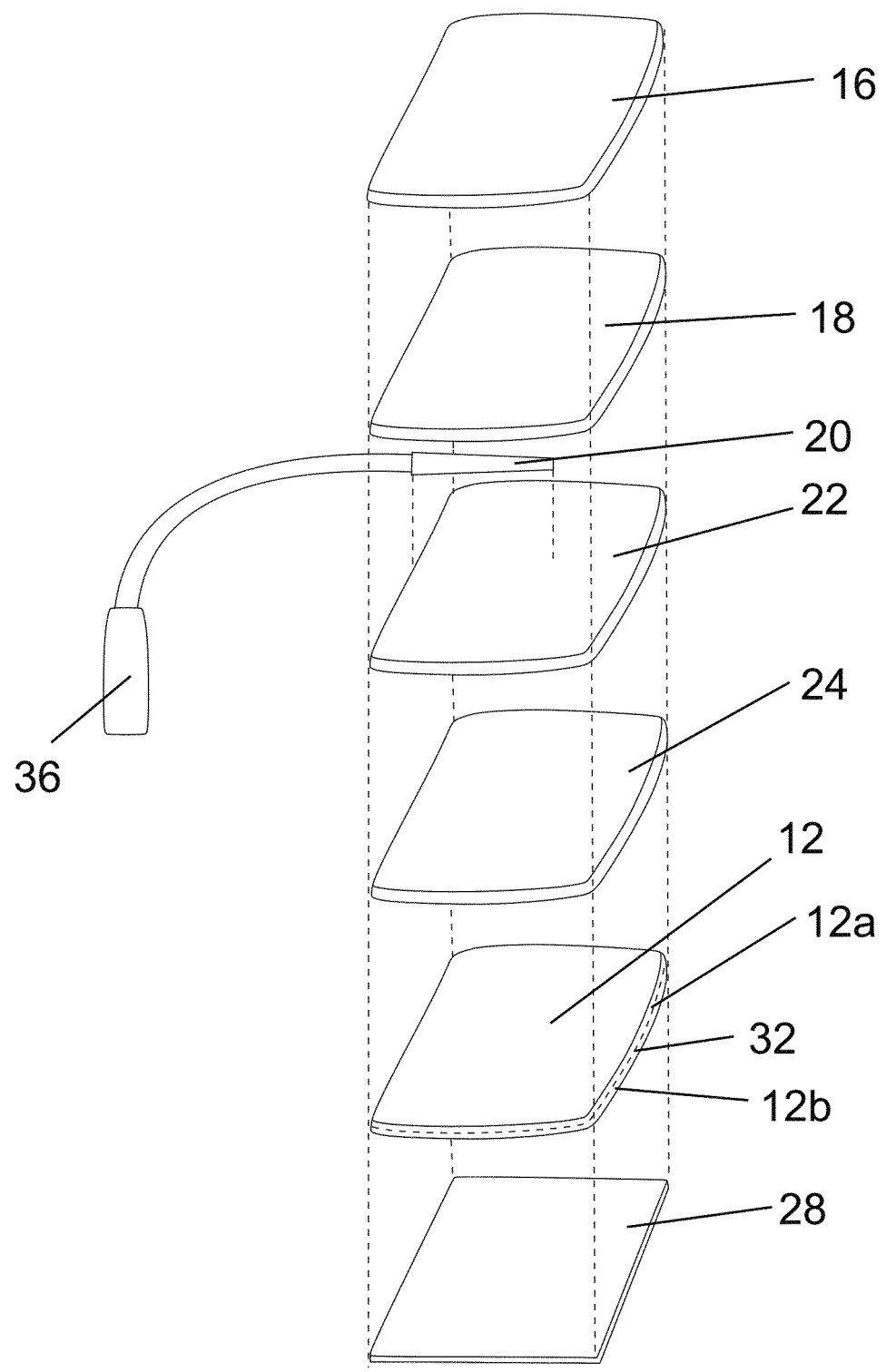
FIG. 3 shows an enlarged detail of FIG. 2.

FIG. 1 shows a top view of an electrode 10 according to an exemplary embodiment of the invention. FIG. 2 shows a cross-sectional view of the electrode 10 of FIG. 1 and FIG. 3 depicts an exploded view of the electrode 10.

As discussed above, the top layer 16 is a cloth and/or foam layer. In one embodiment, the top layer 16 is a cloth layer having a weight of 2.4 ounces, a porosity of about 26,600 lbs./in$^2$, and a tensile strength of about 28,800 lbs./in$^2$. In another embodiment, the top layer 16 is foam. The foam layer has a thickness of about ⅟32", a porosity of about 26,600 lbs./in$^2$, and a tensile strength of about 28,800 lbs./in$^2$. Other types of cloth or foam layers, including those having a different thickness and properties, may be used, as desired. A top layer 16 that is a combination of foam and cloth may also be used. Other types of materials may be used for the top layer 16. For example, a vinyl top layer 16 could be used. Example thicknesses for the top layer may be thickness of ⅟64" to ⅛", or from ⅟32" to ⅟16."

The insulator layer 18, which, in one embodiment, is also an adhesive layer, may be a DM-9006Z transfer adhesive. The insulator layer 18 could simply be an adhesive layer or could be a combination of layers that include an adhesive on an upper and lower surface. The insulator layer 18 helps to hold the electrical lead 20 in place under the insulator layer 18.

The conductive carbon layer 24 may have a thickness of about 0.5 mils to about 5 mils, or about 1 mil to about 4 mils, or about 2 mils to about 3 mils. In one example, the conductive carbon layer 24 has a thickness of about 2.35 mils and no coating (e.g., no silver coating). The tensile strength of the carbon layer 24 may be greater than about 6 lbf. Alternatively, the tensile strength of the conductive carbon layer 24 may be greater than about 3 lbf, greater than about 5 lbf, or greater than about 7 lbf. The conductivity may be less than about 75 ohms/sq. Alternatively, the conductivity may range from about 60 ohms/sq. to about 80 ohms/sq., or about 50 ohms/sq. to 75 ohms/sq. The weight of the carbon layer 24 may be about 74.9 g/m². Alternatively, the weight of the carbon layer may range from about 50 g/m² to about 100 g/m², from 60 g/m² to about 80 gm/m², or from about 70 g/m² to about 75 g/m²

Other types of conductive materials, including those having a different thickness and properties, may be used, as desired. For example, in one embodiment, the insulator layer 18 and conductive layer 24 are manufactured as a single unit, with the insulator layer 18 being an adhesive that is positioned on top of the conductive layer 24. Other types of conductive layers that may be used are known by those of skill in the art. Non-limiting examples of other types of conductive layers include conductive inks, metal mesh, nanowire, metal sputtered layer, graphene, metals, and the like, among other known conductive layers.

The gel layer 12 may be an acrylic hydrogel that has a nominal thickness of about 0.76 mm. The thickness of the hydrogel may range from about 0.1 mm to about 5 mm, or from about 0.2 mm to about 3 mm, or about 0.4 mm to about 2 mm, or from about 0.5 mm to about 1 mm.

A hydrogel is a product that constitutes a group of polymeric materials, the hydrophilic structure of which renders them capable of holding large amounts of water in their three-dimensional networks. A hydrogel is a water-swollen and cross-linked polymeric network produced by the simple reaction of one or more monomers. It is a polymeric material that exhibits the ability to swell and retain a significant fraction of water within its structure but will not dissolve in water. They possess a degree of flexibility that is very similar to natural tissue due to their large water content. Many materials, both naturally occurring and synthetic, fit the definition of hydrogels. The terms gel and hydrogel are used herein interchangeably.

In the present invention, the gel layer comprises two coatings—a thick skin side 12b and a thin tie side 12a. The BEC material is included in the thick skin side 12b to provide the gel layer 12 with anti-microbial properties. A reinforcing mesh may be provided inside the two gel layers 12 to provide a grab sheet tensile strength of about 11 lbs. force in the machine direction (which is the roll winding direction) and about 7 lbs. force in the cross-direction. The mesh material can impart strength or other advantageous properties to the device, as known by those of skill in the art. The mesh material can be embedded in the gel material or can be on the top and/or bottom of the gel material.

The conductivity of the hydrogel layer 12 is about 0.00125 Siemens per centimeter nominal. The volume resistivity is about 800 ohm-cm. 0.2% BEC in powder form is impregnated into the hydrogel to provide the anti-microbial properties to the hydrogel. The mesh layer makes the hydrogel resistant to skin movements during activities as well as when the adhesion drops during sweat build up. The mesh is usually non-conductive. The mesh does not prevent or inhibit the skin contact or comfort of the hydrogel.

One cationic BEC product utilized with the embodiments herein is phemerol chloride that has a titration by AgNO3≥97%, a purity (HPLC)≥98%, and a formula weight of 448.08 g/mol. It has an infrared spectrum that confirms to structure, a solubility (turbidity) that is clear 10 mg/mL, H2O, a colorless solubility (color), a powder appearance (form), a white appearance (color), and a melting point of 162° to 164° C. per liter. This BEC product has the following chemical structure, which contains a positively charged nitrogen atom covalently bonded to four carbon atoms. The positive charge attracts it to the skin and hair and contributes to a soft, powdery after feel on the skin and hair, as well as long-lasting persistent activity against microorganisms.

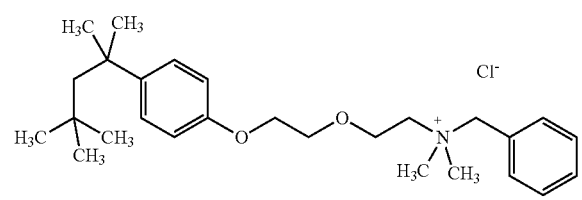

Other types of BEC products may be utilized, such as BioUltra BEC having an assay that is ≥99.0%, a pH of 5.5 to 7.5 (25° C., 0.1M in H2O), and a melting point of 162°–164° C. per liter.

Types of hydrogel that may be utilized with the invention are manufactured by R&D Medical Products, Inc. and are known by the brand names PROMEON and COMFORT Hydrogels. These hydrogels are latex free and are formed from a combination of polyacrylic acid, sodium salt; glycerin; water; and potassium chloride. The hydrogels may be cast onto polyester film, supported by non-woven polyester fabric, and covered with a polyethylene film. PROMEON and COMFORT Hydrogels meet ISO 10993 biocompatibility requirements for skin contact. They are non-cytotoxic, non-irritating, and non-sensitizers.

PROMEON Gel is a hi-tack gel that has a thickness that ranges from about 0.023 to 0.031 inches. Alternatively, the gel may range in thickness from 28 mil to 36 mil. It has an impedance 200 ohms maximum at 10 Hz and a volume resistivity of 1500 ohm-cm maximum. Its adhesion level is 220 grams/in minimum to stainless steel using the PSTC-5 Test method. It is typically non-sensitizing. Another PROMEON Gel has an adhesion strength of 240 grams/in minimum to Stainless steel as measured by PSTC-5 TEST method.

COMFORT Gel has similar properties to PROMEON Gel, with an adhesion of 185 grams/in minimum to stainless steel as measured by the PSTC-5 test method. COMFORT gel may have a thickness similar to that of PROMEON gel, ranging from about 0.023 to 0.031 inches or from 0.028 to 0.036 inches. A level of adhesion for the gel layer will range from about 180 grams/in to about 250 grams/in, from about 185 to 240 grams/in, or from about 185 grams/in to about 220 grams/in.

Other types of gel layers 12, including those having different thicknesses and properties, may be used, as desired. BEC having different concentrations may be utilized, if desired. Other materials having anti-microbial, bacteriostatic, and/or bactericidal properties could be used, if desired. Non-limiting examples of other materials include: salts of chlorhexidine, such as lodopropynyl butylcarbamate, diazolidinyl urea, chlorhexidine digluconate, chlorhexidine acetate, chlorhexidine isethionate, and chlorhexidine hydrochloride; benzalkonium chloride, triclocarban, polyhexamethylene biguanide, cetylpyridium chloride, methyl chloride. halogenated phenolic compounds, such as 2,4,4',-trichloro-2-hydroxy diphenyl ether (Triclosan); parachlorometa xylenol (PCMX); and short chain alcohols, such as ethanol, propanol, and the like.

One type of conductive film layer 24 that may be utilized is a carbon-filled polymeric film Z-FLO™, sold by Coveris Advanced Coatings of Matthews, North Carolina Z-FLO™ is lightweight, low cost and high performing. Z-FLO™ provides "through" conductivity, or conductivity in the z-direction. Z-FLO™ may be in the form of vinyl or silver-coated vinyl.

The BEC component utilized in combination with the hydrogel may be manufactured by Sigma-Aldrich of St. Louis, Missouri under product number B8879. The BEC component, prior to addition to the hydrogel, is in the form of a white powder that has colorless solubility and clear turbidity.

To manufacture the electrode 10, the following steps are utilized:
1) The top carrier layer 16, which may be a cloth and/or foam layer or other layer, is combined with mylar 18 and a sacrificial liner 30.
2) A gel layer 12 and carbon layer 24 are combined separately.
3) Layers created in steps 1 and 2 are combined to create the layered electrode 10.
4) The lowermost layer of gel 12 is married with the polyethylene film backing material 28.
5) The electrode 10 is cut to shape.
6) The electrode sacrificial liner 30 is pulled back and the lead wire 20 is inserted. The sacrificial liner 30 is discarded.
7) The electrode 10 is pressed down to ensure that the lead wire 20 is retained inside the electrode 10.

Electrical lines and leads 20 extend from the electrode 10 to a connector 36. The connector 36 may then be connected to an external control circuit (not shown). While the electrode 10 is described in the context of having pigtail connectors 36, they could alternatively include snap connectors or other connectors known by those of skill in the art.

The carrier layer, or top layer 16, provides mechanical support for the electrode 10 and typically constitutes a body of the electrode 10 that can be handled by a user. The carrier layer 16 is preferably electrically insulating to prevent an uncontrolled spreading of electrical signals from the electrode 10 and to insulate electrodes 10 from each other if several electrodes 10 are disposed on the same carrier 16.

The carrier layer 16 is preferably flexible, thus allowing for an alignment of the electrode 10 to the usually irregular three-dimensional surface of a user's body. The flexibility of the carrier 16 usually means that it can be bent. Additionally or alternatively, the carrier may be stretchable. The electrode 10 can conform to the contours of the subject's body during initial attachment to the subject and can conform to body positioning changes when the subject is in motion.

The addition of the anti-microbial element does not change the electrodes 10 ability to fit all shapes and sizes needed. It continues to allow the electrode 10 to conform to all body parts and movements. In addition, the addition of the anti-microbial does not alter the comfort level of the electrode 10 or limit patient mobility.

The electrode 10 may comprise just a single electrode 10 or a plurality of electrodes 10 that can independently be connected to and/or controlled by an external circuit. The electrode 10 can be compliant with the American National Standards Institute (ANSI) standards for electrodes 10, or with the Association for the Advancement of Medical Instrumentation (AAMI) standards for electrodes 10.

Zone of Inhibition testing was performed to determine the efficacy of the anti-microbial gel layer 12 of the electrode 10. Zone of inhibition testing is a fast, qualitative way to measure the ability of an antimicrobial agent to inhibit the growth of microorganisms. In some cases, a zone of inhibition 14 is a zone where the microorganisms are killed. In other cases, the zone of inhibition 14 is an area where growth of the microorganism is prevented. When multiple microorganisms are present, the zone of inhibition 14 may include killing some of the microorganisms and inhibiting growth of other microorganisms. The term "zone of inhibition" is meant to encompass both definitions, either individually or in combination.

A Zone of Inhibition Test, also called a Kirby-Bauer Test, is a qualitative method used clinically to measure antibiotic resistance and industrially to test the ability of solids and textiles to inhibit microbial growth. With this method, approximately one million cells from a single strain are spread over an agar plate using a sterile swab, then incubated in the presence of an antimicrobial object. If the bacterial or fungal strain is susceptible to the antimicrobial agent, then a zone of inhibition 14 appears on the agar plate. If it is resistant to the antimicrobial agent, then no zone will be evident. If the antimicrobial agent leaches from the object into the agar and then exerts a growth-inhibiting effect, then a clear zone (the zone of inhibition 14) appears around the test object.

The size of the zone of inhibition 14 is usually related to the level of antimicrobial activity present in the sample or product. A larger zone of inhibition 14 usually means that the antimicrobial is more potent. Zone of inhibition testing is especially well suited for determining the ability of water-soluble antimicrobials to inhibit the growth of microorganisms. Zone of inhibition tests do not necessarily mean that the microorganisms have been killed by the antimicrobial product, just that they have been prevented from growing. In some instances, however, the antimicrobial can kill the microorganism.

EXAMPLES

The following testing conditions were utilized in evaluating the Examples described herein. Microchem Laboratory of Round Rock, Texas was utilized for testing. The purpose of the testing was to evaluate the ability of the control product (Promeon M862 Gel) and the test product (Anti-microbial Gel) to inhibit the growth of the test microorganisms using the zone of inhibition (Kirby-Bauer) test and the AATCC 100 method to simulate the effects of the antimicrobial agents on electrode pads 12. The form of the anti-microbial gel was an acrylic hydrogel having an active ingredient of 0.2% Benzethonium Chloride (BEC) in the shape of a coupon 40.

The zone of inhibition was determined to be no larger than 5.65 mm for the anti-microbial gel and no larger than 4.40 mm for the Promeon M862 Gel. No growth of the test microorganisms was demonstrated under any of the test or control substance coupons. The anti-microbial gel demonstrated $\log_{10}$ reductions between 5.68 and 4.96 compared to the initial number controls. The Promeon M862 Gel demonstrated $\log_{10}$ reductions between 5.42 and 1.13 compared to the initial numbers control.

The following test microorganisms were tested:
*E. cloacae* ATCC BAA-2468 (CRE)
*S. aureus* ATCC 33592 (MRSA)
*E. coli* ATCC BAA-196 (ESBL)
*E. faecalis* ATCC 51575 (VRE)

*P. aeruginosa* ATCC BAA-2114 (Multi-Drug Resistant)

*A. baumannii* ATCC BAA-1605 (Multi-Drug Resistant)

All of these microorganisms are known to cause infectious disease in mammals.

Two different tests methods were used. A first test method was AATCC 100 anti-microbial textile testing and a second method was Zone of Inhibition testing.

For the first test method, 18 tests were performed—one test substance, two control substances, and six microorganisms. The inoculum target concentration was $\geq 1 \times 10^6$ CFU/dressing. The inoculum volume was 0.5 ml. The test involved the use of simulated would fluid to determine whether the antimicrobial gel exhibits a zone of inhibition on the skin. The simulated would fluid was comprised of 5.0±0.2% Bovine Serum Albumin, 142±5 mM Sodium Chloride, and 2.5±mM Calcium Chloride. A coupon was positioned on the simulated wound fluid for 24±1 hour. The coupon size was approximately 2"×1".

The contact temperature was 36±1° C. The neutralizer/recovery medium was Dey Engley Broth (20 ml). The number of test replicates was 3. The plating medium was tryptic soy agar. The enumeration plate incubation conditions were 36±1° C. for 48±6 hours.

The study parameters for the Zone of Inhibition testing were as follows: There were 12 tests, including one test substance, one control substance and six microorganisms. The swab target concentration was $\geq 1 \times 10^6$ CFU/ml. The inoculation method was swab inoculation. The coupon size was approximately 2"×1". The contact time was 24±1 hour. The contact temperature was 36±1° C. The number of test replicates was 3. The plating medium was tryptic soy agar. The enumeration plate conditions were 36±1° C. for 48±6 hours.

The ability of the test and control substances to inhibit growth of microorganisms and kill microorganisms was evaluated. Inhibition of growth under the test and control substance coupons, as well as around the coupons, were evaluated.

The controls included the following:

Phosphate Buffered Saline Sterility Control—An aliquot of each lot of P35 used was pour plated to assess sterility. This control was conducted to ensure that the dilution media were free of contaminating microorganisms.

Neutralizer/Recovery Medium Sterility Control—An aliquot of Dey Engley Broth was pour-plated to assess sterility. This control was conducted to ensure that the neutralizer/recovery medium did not contain contaminating microorganisms.

Simulated Wound Fluid Sterility Control—An aliquot of SWF was poured plated to assess sterility. This control was conducted to ensure that the AATCC 100 inoculum diluent did not contain contaminating microorganisms.

Plating Media Sterility Control—Each lot of growth agar was poured into a sterile Petri dish and incubated alongside enumeration plates. This control was conducted to ensure that the plating medium was adequately sterilized and remained sterile until use in the study.

Neutralization Verification—The neutralization media was assessed for its ability to neutralize the active antimicrobial agent of the test substance. The anti-microbial gel and Promeon gel were both put into individual tubes of Dey Engley Broth and vortex mixed. Aliquots were removed from both tubes and individually inoculated with test microorganisms. The inoculated aliquots were allowed to sit for a minimum of 10 minutes. The aliquots were then pour-plated with TSA. This control was performed to ensure that the antimicrobial agent was adequately neutralized by the neutralization medium, so as to stop the contact time as soon as the test substance was introduced to the neutralization medium and to adequately recover any microorganisms that were still viable.

Positive Growth Control—A positive growth control of each test microorganism was performed. A sterile swab was dipped into the diluted test inoculum and struck to a sterile Petri dish in the same fashion as inoculating zone of inhibition test plates. These controls were incubated alongside the test plates and used as a positive growth comparison for the zones of inhibition.

Test Microorganism Purity/Growth Control—A viability streak of each microorganism involved in the test was performed by taking a loopful of the overnight liquid culture and streaking it to growth agar as appropriate to achieve isolated colonies. This control confirmed that the microorganisms used in the test were viable for growth, pure in their culturing, that the broth media was sterile, and that the growth agar promoted growth of the test microorganisms.

Enumeration of Test Inocula—The test inocula for each microorganism was enumerated to confirm the concentration. The inocula for both the zone of inhibition and AATCC 100 were enumerated.

Enumeration of Swabs—One swab was dipped in the test inoculum for each microorganism, used to inoculate three test or control plates, and then harvested in sterile PBS to be enumerated. The harvested swabs were individually enumerated using standard enumeration and plating techniques.

The experimental success controls criteria included:

1) all media sterility controls must be negative for growth of the test microorganisms;
2) the viability controls must be positive for growth of the test microorganisms;
3) the neutralization test suspension count must be $\geq 70\%$ of that recorded for the neutralization control suspension count;
4) the test microorganism concentration obtained from the neutralization verification control suspension must demonstrate a test microorganism count of approximately 5-100 CFU;
5) initial numbers control dressings must demonstrate a starting concentration of $\geq 1 \times 10_6$ CFU/dressing; and
6) swabs used for inoculating test plates must demonstrate $\geq 1 \times 10_4$ CFU/swab.

The study acceptance product performance criteria for the testing required demonstration of a 4 $\log_{10}$ for topical skin dressing to be considered efficacious against a microorganism.

The following calculations were used:

Colony Forming Units per ml—

$$[(\text{Plate count 1} + \text{plate count 2})/2] * \text{dilution factor} = \text{CFU/ml}$$

Colony Forming Units per dressing or per swab—

$$[(\text{Plate count 1} + \text{plate count 2})/2] * \text{dilution factor} = \text{CFU/dressing or swab}$$

Percent Reduction—

$$P_1 = 100[(B-A)/B]$$

where:

$P_1$=Percent Reduction

A=the mean number of surviving microorganisms on the test dressings

B=the mean number of surviving microorganisms on inoculated control dressings

Log Reduction—

$$L_1 = \log(B/A)$$

where:
$L_1$ = Log Reduction
A = the mean number of surviving microorganisms on the test dressings
B the mean number of surviving microorganisms on inoculated control dressings Average Width of a Zone of Inhibition—

$$W = (T-D)/2$$

where:
W = width of clear zone of inhibition in mm
T = total width of test specimen and clear zone in mm
D = width of the test specimen in mm The following results, shown in Tables 1-15, were obtained:

TABLE 1

Percent and $\log_{10}$ reductions for the test and control substances against *E. cloacae* ATCC BAA-2468 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| *E. cloacae* ATCC BAA-2468 | Initial Numbers Control | Microchem Control | 1 | 8.70E+06 | 9.53E+06 | N/A | | | |
| | | | 2 | 9.80E+06 | | | | | |
| | | | 3 | 1.01E+07 | | | | | |
| | 24 Hours | | 1 | 7.81E+08 | 9.72E+08 | | | | |
| | | | 2 | 1.19E+09 | | | | | |
| | | | 3 | 9.48E+06 | | | | | |
| | | Promeon M862 Gel | 1 | 1.40E+02 | 5.67E+01 | 99.9994% | 5.23 | 99.999994% | 7.23 |
| | | | 2 | 2.00E+01 | | | | | |
| | | | 3 | 1.00E+01 | | | | | |
| | | Antimicrobial Gel | 1 | 3.00E+01 | <2.00E+01 | >99.9998% | >5.68 | >99.999998% | >7.69 |
| | | | 2 | 2.00E+01 | | | | | |
| | | | 3 | <10 | | | | | |

Note:
The limit of detection is 10 CFU/carrier. If no microorganisms were recovered from a dressing, the result is displayed as <10. If a replicate had a concentration of <10 CFU/carrier, then a value of 10 was used to calculate the Average CFU/carrier.

TABLE 2

Percent and $\log_{10}$ reductions for the test and control substances against *S. aureus* ATCC 33592 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| *S. aureus* ATCC 33592 | Initial Numbers Control | Microchem Control | 1 | 9.50E+06 | 8.13E+06 | N/A | | | |
| | | | 2 | 6.70E+06 | | | | | |
| | | | 3 | 8.20E+06 | | | | | |
| | 24 Hours | | 1 | 6.20E+07 | 8.17E+07 | | | | |
| | | | 2 | 1.04E+08 | | | | | |
| | | | 3 | 5.90E+07 | | | | | |
| | | Promeon M862 Gel | 1 | 4.90E+04 | 6.37E+04 | 99.22% | 2.11 | 99.92% | 3.11 |
| | | | 2 | 3.00E+04 | | | | | |
| | | | 3 | 1.12E+05 | | | | | |
| | | Antimicrobial Gel | 1 | 5.00E+01 | 1.03E+02 | 99.9987% | 4.90 | 99.99987% | 5.90 |
| | | | 2 | 1.20E+02 | | | | | |
| | | | 3 | 1.40E+02 | | | | | |

Note:
The limit of detection is 10 CFU/carrier. If no microorganisms were recovered from a dressing, the result is displayed as <10. If a replicate had a concentration of <10 CFU/carrier, then a value of 10 was used to calculate the Average CFU/carrier.

TABLE 3

Percent and $\log_{10}$ reductions for the test and control substances against *E. coli* ATCC BAA-196 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| *E. coli* ATCC BAA-196 | Initial Numbers Control | Microchem Control | 1 | 8.20E+06 | 7.86E+06 | N/A | | | |
| | | | 2 | 7.50E+06 | | | | | |
| | | | 3 | 7.90E+06 | | | | | |
| | 24 Hours | | 1 | 2.07E+08 | 2.11E+08 | | | | |
| | | | 2 | 2.38E+08 | | | | | |
| | | | 3 | 1.88E+08 | | | | | |
| | | Promeon M862 Gel | 1 | 2.00E+01 | 3.00E+01 | 99.9996% | 5.42 | 99.999986% | 6.85 |
| | | | 2 | 1.00E+01 | | | | | |
| | | | 3 | 6.00E+01 | | | | | |
| | | Anti-microbial Gel | 1 | <10 | <1.67E+01 | >99.9997% | >5.67 | >99.999992 | >7.10 |
| | | | 2 | <10 | | | | | |
| | | | 3 | 3.00E+01 | | | | | |

Note:
The limit of detection is 10 CFU/carrier. If no microorganisms were recovered from a dressing, the result is displayed as <10. If a replicate had a concentration of <10 CFU/carrier, then a value of 10 was used to calculate the Average CFU/carrier.

TABLE 4

Percent and $\log_{10}$ reductions for the test and control substances against *E. faecalis* ATCC 51575 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| *E. faecalis* ATCC 51575 | Initial Numbers Control | Microchem Control | 1 | 1.13E+07 | 9.97E+06 | N/A | | | |
| | | | 2 | 7.80E+06 | | | | | |
| | | | 3 | 1.10E+07 | | | | | |
| | 24 Hours | | 1 | 8.00E+07 | 7.63E+07 | | | | |
| | | | 2 | 7.50E+07 | | | | | |
| | | | 3 | 8.00E+07 | | | | | |
| | | Promeon M862 Gel | 1 | 3.20E+05 | 7.44E+05 | 92.54% | 1.13 | 99.05% | 2.02 |
| | | | 2 | 6.68E+05 | | | | | |
| | | | 3 | 1.24E+06 | | | | | |
| | | Anti-microbial Gel | 1 | 1.30E+02 | 1.10E+02 | 99.9989% | 4.96 | 99.99986% | 5.86 |
| | | | 2 | 1.00E+01 | | | | | |
| | | | 3 | 1.90E+02 | | | | | |

Note:
The limit of detection is 10 CFU/carrier. If no microorganisms were recovered from a dressing, the result is displayed as <10. If a replicate had a concentration of <10 CFU/carrier, then a value of 10 was used to calculate the Average CFU/carrier.

TABLE 5

Percent and $\log_{10}$ reductions for the test and control substances against *P. aeruginosa* ATCC BAA-2114 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| *P. aeruginosa* ATCC BAA-2114 | Initial Numbers Control | Microchem Control | 1 | 1.30E+06 | 1.32E+06 | N/A | | | |
| | | | 2 | 1.43E+06 | | | | | |
| | | | 3 | 1.22E+06 | | | | | |
| | 24 Hours | | 1 | 8.32E+08 | 6.34E+08 | | | | |
| | | | 2 | 7.16E+08 | | | | | |
| | | | 3 | 3.53E+08 | | | | | |

TABLE 5-continued

Percent and log$_{10}$ reductions for the test and control substances against *P. aeruginosa* ATCC BAA-2114 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| | | Promeon M862 Gel | 1 | <10 | <1.63E+02 | >99.988% | >3.91 | >99.99997% | >6.59 |
| | | | 2 | 4.70E+02 | | | | | |
| | | | 3 | <10 | | | | | |
| | | Anti-microbial Gel | 1 | <10 | <1.00E+01 | >99.9992% | >5.12 | >99.999998% | >7.80 |
| | | | 2 | <10 | | | | | |
| | | | 3 | 1.00E+01 | | | | | |

Note:
The limit of detection is 10 CFU/carrier. If no microorganisms were recovered from a dressing, the result is displayed as <10. If a replicate had a concentration of <10 CFU/carrier, then a value of 10 was used to calculate the Average CFU/carrier.

TABLE 6

Percent and log$_{10}$ reductions for the test and control substances against *A. baumannii* ATCC BAA-1605 compared to the initial numbers control and parallel Microchem Control

| Microorganisms | Challenge Time | Test Surface | Replicate | Replicate CFU/carrier | Average CFU/carrier | Percent Reduction vs. Initial Numbers Control | Log reduction vs. Initial Numbers Control | Percent Reduction vs. Microchem Control | Log reduction vs. Microcham Control |
|---|---|---|---|---|---|---|---|---|---|
| *A. baumannii* ATCC BAA-1605 | Initial Numbers Control | Microchem Control | 1 | 2.72E+06 | 2.43E+06 | | N/A | | |
| | | | 2 | 2.09E+06 | | | | | |
| | | | 3 | 2.48E+06 | | | | | |
| | 24 Hours | | 1 | 4.57E+08 | 6.38E+08 | | | | |
| | | | 2 | 7.02E+08 | | | | | |
| | | | 3 | 7.55E+08 | | | | | |
| | | Promeon M862 Gel | 1 | 2.19E+02 | 8.00E+01 | 99.9997% | 4.48 | 99.999987% | 6.90 |
| | | | 2 | 1.00E+01 | | | | | |
| | | | 3 | 2.00E+01 | | | | | |
| | | Anti-microbial Gel | 1 | 1.00E+01 | 2.33E+01 | 99.9990% | 5.02 | 99.999996% | 7.44 |
| | | | 2 | 5.00E+01 | | | | | |
| | | | 3 | 1.00E+01 | | | | | |

Note:
The limit of detection is 10 CFU/carrier. If no microorganisms were recovered from a dressing, the result is displayed as <10. If a replicate had a concentration of <10 CFU/carrier, then a value of 10 was used to calculate the Average CFU/carrier.

TABLE 7

Zones of Inhibition

| Test Substance | Microorganism | Replicate | Width of Specimen Before Contact Time (mm) | Width of Specimen After Contact Time (mm) | Width of Clear Zone of Inhibition (mm) | Average Zone of Inhibition Size (mm) | Growth of Test Microorganism Under Test Coupon |
|---|---|---|---|---|---|---|---|
| Anti-microbial Gel | *E. cloacae* ATCC BAA-2468 | 1 | 25.0 | 31.6 | 31.6 | 0.00 | No |
| | | 2 | 24.2 | 29.5 | 29.5 | 0.00 | No |
| | | 3 | 23.2 | 29.6 | 29.6 | 0.00 | No |
| | *S. aureus* ATCC 33592 | 1 | 24.4 | 26.7 | 38.0 | 5.65 | No |
| | | 2 | 23.0 | 25.8 | 35.3 | 4.75 | No |
| | | 3 | 24.9 | 27.5 | 38.2 | 5.35 | No |
| | *E. coli* ATCC BAA-196 | 1 | 25.0 | 28.3 | 31.5 | 1.60 | No |
| | | 2 | 24.1 | 27.1 | 29.8 | 1.35 | No |
| | | 3 | 25.3 | 27.6 | 31.6 | 2.00 | No |
| | *E. faecalis* ATCC 51575 | 1 | 22.6 | 24.8 | 33.6 | 4.40 | No |
| | | 2 | 24.2 | 26.5 | 31.7 | 2.60 | No |
| | | 3 | 23.9 | 25.1 | 32.6 | 3.75 | No |
| | *P. aeruginosa* ATCC BAA-2114 | 1 | 23.7 | 25.4 | 26.5 | 0.55 | No |
| | | 2 | 23.0 | 23.8 | 27.5 | 1.85 | No |
| | | 3 | 25.1 | 26.6 | 28.9 | 1.15 | No |
| | *A. baumannii* | 1 | 24.2 | 27.6 | 28.3 | 0.35 | No |

TABLE 7-continued

Zones of Inhibition

| Test Substance | Microorganism | Replicate | Width of Specimen Before Contact Time (mm) | Width of Specimen After Contact Time (mm) | Width of Clear Zone of Inhibition (mm) | Average Zone of Inhibition Size (mm) | Growth of Test Microorganism Under Test Coupon |
|---|---|---|---|---|---|---|---|
| | ATCC BAA-1605 | 2 | 24.9 | 27.6 | 29.0 | 0.70 | No |
| | | 3 | 22.9 | 24.4 | 26.2 | 0.90 | No |
| Promeon M862 Gel | E. cloacae ATCC BAA-2468 | 1 | 23.9 | 26.9 | 26.9 | 0.00 | No |
| | | 2 | 25.1 | 29.1 | 29.1 | 0.00 | No |
| | | 3 | 23.5 | 28.5 | 28.5 | 0.00 | No |
| | S. aureus ATCC 33592 | 1 | 23.1 | 26.9 | 29.2 | 1.15 | No |
| | | 2 | 24.9 | 27.3 | 33.0 | 2.85 | No |
| | | 3 | 26.0 | 28.6 | 37.4 | 4.40 | No |
| | E. coli ATCC BAA-196 | 1 | 24.2 | 25.0 | 28.4 | 1.70 | No |
| | | 2 | 22.0 | 23.7 | 26.1 | 1.20 | No |
| | | 3 | 24.7 | 26.1 | 28.0 | 0.95 | No |
| | E. faecalis ATCC 51575 | 1 | 23.9 | 25.8 | 27.8 | 1.00 | No |
| | | 2 | 25.2 | 26.2 | 28.5 | 1.15 | No |
| | | 3 | 24.5 | 25.5 | 27.4 | 0.95 | No |
| | P. aeruginosa ATCC BAA-2114 | 1 | 24.5 | 25.0 | 27.9 | 1.45 | No |
| | | 2 | 23.5 | 25.7 | 26.6 | 0.45 | No |
| | | 3 | 22.6 | 24.1 | 25.2 | 0.55 | No |
| | A. baumannii ATCC BAA-1605 | 1 | 23.9 | 25.0 | 25.0 | 0.00 | No |
| | | 2 | 24.0 | 27.4 | 27.4 | 0.00 | No |
| | | 3 | 23.7 | 25.0 | 25.0 | 0.00 | No |

Note:
The width of the specimen after the contact time was the value used to calculate the Average Zone of Inhibition Size.

TABLE 8

Enumeration of AATCC 100 Test Inocula

| Microorganism | Sample Type | CFU/ml |
|---|---|---|
| E. cloacae ATCC BAA-2468 | AATCC 100 Test Inocula | 2.74E+07 |
| S. aureus ATCC 33592 | | 1.25E+07 |
| E. coli ATCC BAA-196 | | 3.05E+07 |
| E. faecalis ATCC 51575 | | 3.45E+07 |
| P. aeruginosa ATCC BAA-2114 | | 1.15E+06 |
| A. baumannii ATCC BAA-1605 | | 1.80E+06 |

TABLE 9

Enumeration of ZOI Test Inocula and Swabs used to inoculate plates

| Microorganism | Sample Type | CFU/ml (for inocula) or CFU/swab |
|---|---|---|
| E. cloacae ATCC BAA-2468 | ZOI Test Inoculum | 1.73E+08 |
| | Swab | 1.55E+07 |
| S. aureus ATCC 33592 | ZOI Test Inoculum | 4.80E+07 |
| | Swab | 9.20E+06 |
| E. coli ATCC BAA-196 | ZOI Test Inoculum | 1.53E+08 |
| | Swab | 1.35E+07 |
| E. faecalis ATCC 51575 | ZOI Test Inoculum | 1.45E+08 |
| | Swab | 8.55E+06 |
| P. aeruginosa ATCC BAA-2114 | ZOI Test Inoculum | 2.90E+07 |
| | Swab | 1.60E+06 |
| A. baumannii ATCC BAA-1605 | ZOI Test Inoculum | 3.85E+07 |
| | Swab | 4.90E+06 |

TABLE 10

Incubation of test substances and enumeration plates

| Sample Type | Incubation Temperature | Date Plates Placed in Incubator | Incubation Duration |
|---|---|---|---|
| ZOI Test Plates | 36 ± 1° C. | 24 Oct. 2018 | 23 h 01 min |
| ZOI Enumeration Plates | | 24 Oct. 2018 | 42 h 05 min |
| AATCC 100 Test Coupons | | 24 Oct. 2018 | 23 h 01 min |
| AATCC 100 Enumeration Plates | | 24 Oct. 2018 | 42 h 05 min |
| AATCC 100 Enumeration Plates | | 25 Oct. 2018 | 43 h 19 min |

TABLE 11

Neutralization Verification for both test substances

| Microorganism | NV Control Count | NV count for Promeon M862 | NV count for Anti-microbial Gel | ≥70% of NV counts vs. NV Control Counts for Promeon M862? | ≥70% of NV counts vs. NV Control Counts for Anti-Microbial Gel? |
|---|---|---|---|---|---|
| E. cloacae ATCC BAA-2468 | 37 | 36 | 36 | Yes | Yes |
| S. aureus ATCC 33592 | 14 | 14 | 19 | Yes | Yes |

TABLE 11-continued

Neutralization Verification for both test substances

| Microorganism | NV Control Count | NV count for Promeon M862 | NV count for Anti-microbial Gel | ≥70% of NV counts vs. NV Control Counts for Promeon M862? | ≥70% of NV counts vs. NV Control Counts for Anti-Microbial Gel? |
|---|---|---|---|---|---|
| E. coli ATCC BAA-196 | 41 | 47 | 42 | Yes | Yes |
| E. faecalis ATCC 51575 | 30 | 32 | 32 | Yes | Yes |
| P. aeruginosa ATCC BAA-2114 | 12 | 13 | 11 | Yes | Yes |
| A. baumannii ATCC BAA-1605 | 10 | 12 | 16 | Yes | Yes |

TABLE 12

Initiation and incubation of test cultures

| Sample Type | Incubation Temperature | Date Cultures Inoculated | Incubation Duration |
|---|---|---|---|
| E. cloacae ATCC BAA-2468 | 36 ± 1° C. | 23 Oct. 2018 | 22 h 52 m |
| S. aureus ATCC 33592 | | | |
| E. coli ATCC BAA-196 | | | |
| E. faecalis ATCC 51575 | | | |
| P. aeruginosa ATCC BAA-2114 | | | |
| A. baumannii ATCC BAA-1605 | | | |

TABLE 13

Sterility, viability, and positive controls

| Date Control Conducted | Control Type Assessed | Positive or Negative for Growth |
|---|---|---|
| 24 Oct. 2018 | Phosphate Buffered Saline | Negative |
| 24 Oct. 2018 | Simulated Wound Fluid | Negative |
| 24 Oct. 2018 | Neutralization Broth | Negative |
| 24 Oct. 2018 | Tryptic Soy Agar | Negative |
| 24 Oct. 2018 | E. cloacae ATCC BAA-2468 Purity Streak | Positive, Pure |
| 24 Oct. 2018 | S. aureus ATCC 33592 Purity Streak | Positive, Pure |
| 24 Oct. 2018 | E. coli ATCC BAA-196 Purity Streak | Positive, Pure |
| 24 Oct. 2018 | E. faecalis ATCC 51575 Purity Streak | Positive, Pure |
| 24 Oct. 2018 | P. aeruginosa ATCC BAA-2114 Purity Streak | Positive, Pure |
| 24 Oct. 2018 | A. baumannii ATCC BAA-1605 Purity Streak | Positive, Pure |
| 24 Oct. 2018 | E. cloacae ATCC BAA-2468 Positive Control | Positive |
| 24 Oct. 2018 | S. aureus ATCC 33592 Positive Control | Positive |
| 24 Oct. 2018 | E. coli ATCC BAA-196 Positive Control | Positive |
| 24 Oct. 2018 | E. faecalis ATCC 51575 Positive Control | Positive |
| 24 Oct. 2018 | P. aeruginosa ATCC BAA-2114 Positive Control | Positive |
| 24 Oct. 2018 | A. baumannii ATCC BAA-1605 Positive Control | Positive |
| 25 Oct. 2018 | Phosphate Buffered Saline | Negative |
| 25 Oct. 2018 | Tryptic Soy Agar | Negative |
| 6 Nov. 2018 | Mueller Hinton Agar | Negative |
| 6 Nov. 2018 | Tryptic Soy Agar | Negative |
| 6 Nov. 2018 | Phosphate Buffered Saline | Negative |
| 6 Nov. 2018 | E. cloacae ATCC BAA-2468 Positive Control | Positive |
| 6 Nov. 2018 | S. aureus ATCC 33592 Positive Control | Positive |
| 6 Nov. 2018 | E. coli ATCC BAA-196 Positive Control | Positive |
| 6 Nov. 2018 | E. faecalis ATCC 51575 Positive Control | Positive |
| 6 Nov. 2018 | P. aeruginosa ATCC BAA-2114 Positive Control | Positive |
| 6 Nov. 2018 | A. baumannii ATCC BAA-1605 Positive Control | Positive |
| 6 Nov. 2018 | E. coli ATCC 25922 Positive Control | Positive |
| 6 Nov. 2018 | S. aureus ATCC 25923 Positive Control | Positive |
| 6 Nov. 2018 | E. coli ATCC 35218 Positive Control | Positive |
| 6 Nov. 2018 | P. aeruginosa ATCC 27853 Positive Control | Positive |
| 6 Nov. 2018 | E. cloacae ATCC BAA-2468 Purity Streak | Positive, Pure |
| 6 Nov. 2018 | S. aureus ATCC 33592 Purity Streak | Positive, Pure |

TABLE 13-continued

Sterility, viability, and positive controls

| Date Control Conducted | Control Type Assessed | Positive or Negative for Growth |
|---|---|---|
| 6 Nov. 2018 | E. coli ATCC BAA-196 Purity Streak | Positive, Pure |
| 6 Nov. 2018 | E. faecalis ATCC 51575 Purity Streak | Positive, Pure |
| 6 Nov. 2018 | P. aeruginosa ATCC BAA-2114 Purity Streak | Positive, Pure |
| 6 Nov. 2018 | A. baumannii ATCC BAA-1605 Purity Streak | Positive, Pure |
| 6 Nov. 2018 | E. coli ATCC 25922 Purity Streak | Positive, Pure |
| 6 Nov. 2018 | S. aureus ATCC 25923 Purity Streak | Positive, Pure |
| 6 Nov. 2018 | E. coli ATCC 35218 Purity Streak | Positive, Pure |
| 6 Nov. 2018 | P. aeruginosa ATCC 27853 Purity Streak | Positive, Pure |

TABLE 14

Baseline microbial load of representative test and control coupons before testing

| Test Surface | Replicate | Replicate CFU/carrier | Average CFU/carrier |
|---|---|---|---|
| Microchem Control | 1 | 1.70E+04 | 1.06E+04 |
| | 2 | 6.99E+03 | |
| | 3 | 7.87E+03 | |
| Promeon MB62 Gel | 1 | 1.50E+02 | 1.63E+02 |
| | 2 | 1.10E+02 | |
| | 3 | 2.30E+02 | |
| Anti-microbial Gel | 1 | 7.00E+01 | 6.00E+01 |
| | 2 | 6.00E+01 | |
| | 3 | 5.00E+01 | |

TABLE 15

Antibiotic Susceptibility of the Test Microorganisms

| Test Microorganism | Reference Microorganism | Antibiotic | Diameter Range Demonstrating Susceptibility | Diameter Range Demonstrating Resistance | Test Microorganism Diameter | Reference Microorganism Diameter | Test Microorganism Demonstrates Resistance? |
|---|---|---|---|---|---|---|---|
| E. cloacae ATCC BAA-2468 | E. coli ATCC 25922 | Piperacillin | ≥21 mm | ≤17 mm | 6.5 mm | 25.3 mm | Yes |
| S. aureus ATCC 33592 | S. aureus ATCC 25923 | Oxocillin | ≥13 mm | ≤10 mm | 9.2 mm | 51.9 mm | Yes |
| E. coli ATCC BAA-196 | E. coli ATCC 35218 | Piperacillin-tazobactam | ≥21 mm | ≤17 mm | 27.7 mm | 27.9 mm | Inconclusive |
| E. faecalis ATCC 51575 | S. aureus ATCC 25923 | Vancomycin | ≥17 mm | ≤14 mm | 11.3 mm | 21.2 mm | Yes |
| P. aeruginosa ATCC BAA-2114 | E. coli ATCC 35218 | Piperacillin-tazobactam | ≥21 mm | ≤14 mm | 31.1 mm | 27.0 mm | Inconclusive |
| A. baumannii ATCC BAA-1605 | P. aeruginosa ATCC 27853 | Piperacillin | ≥21 mm | ≤17 mm | 6.5 mm | 26.2 mm | Yes |

Note:
For the test microorganisms that did not show resistance, further characterization may be required. ATCC certifies that all microorganisms with a claim of resistance contain the appropriate genes to exhibit resistance. This proof of genetic material is maintained by ATCC. The diameter ranges that determine resistance or susceptibility are provided in M100 from CLSI (see reference 2 in the References section of this report).

A test protocol was followed, which included preparation and handling of test and control substances. Test and control hydrogel substances were subjected to simulated use cycles involving 10 contacts for 30 minutes with human skin. The substances were handled aseptically so as to not add environmental contamination. The substances were aseptically cut in half. One half of each dressing was used for the AATCC 100 while the other half was used for the Zone of Inhibition testing. A control was used to perform an initial numbers control and parallel control for the AATCC 100. The control materials was sterilized untreated cotton fabric. The swatches were approximately 2"×6".

An incubation method of swab incubation was utilized at a swab target concentration of ≥1×10$^6$ CFU/ml. Contact time was 24±1 hour. Test temperature was 36±1° C. The test and control carrier size was a 2×2 cm (±2 mm) coupon for all test substances. The plating medium was Tryptic Soy Agar 44 in a petri dish 46. The culturing medium was Tryptic Soy Broth. The enumeration plate incorporation conditions were 36±1° C. for 24±1 hour.

The test was conducted following Testing protocol 2172 with the Kirby-Bauer Test method. The protocol followed the Zone of Inhibition method where the ability of the test and control substances to inhibit the grown of the microorganisms was evaluated. Inhibition of growth under the test and control substance coupons as well as around the coupons were evaluated.

The test substance Anti-microbial Gel and control substance Promeon M862 Gel were aseptically cut into coupons (not shown), placed on inoculated agar 44 plates in petri dishes 46, and allowed to incubate for 24±1 hours at 36±1° C. Growth of the test microorganisms was evaluated under each test or control substance coupon as well as around each coupon.

The observed average zones of inhibition formed by the Anti-microbial gel test substance around the coupon were as follows:
- 5.25 mm for *S. aureus* ATCC 33592 (MRSA)
- 1.68 mm for *E. coli* ATCC BAA-196 (ESBL)
- 3.58 mm for *E. faecalis* ATCC 51575 (VRE)
- 1.18 mm for *P. aeruginosa* ATCC BAA-2114 (Multi-Drug Resistant)
- 0.65 mm for *A. baumannii* ATCC BAA-1605 (Multi-Drug Resistant)

The Anti-microbial Gel did not form a zone of inhibition 14 with *E. cloacae* ATCC BAA-2468 (CRE). The Promeon M862 Gel control substance formed a zone of inhibition 14 as follows:
- 2.8 mm for *S. aureus* ATCC 33592 (MRSA)
- 1.28 mm for *E. coli* ATCC BAA-196 (ESBL)
- 1.0 mm for *E. faecalis* ATCC 51575 (VRE)
- 0.82 mm for *P. aeruginosa* ATCC BAA-2114 (Multi-Drug Resistant)

The Promeon Gel did not form a zone of inhibition with *E. cloacae* ATCC BAA-2468 (CRE) or *A. baumannii* ATCC BAA-1605 (Multi-Drug Resistant). Both the test and control substances prevented growth of all test microorganisms where each coupon remained in contact with the agar 44 (under each coupon).

The Anti-Microbial gel performed better than the Promeon gel in all instances except for with *E. cloacae* ATCC BAA-2468 (CRE), where the gels were equal in that neither produced a Zone of Inhibition. The following difference in performance were identified, with the Anti-Microbial Gel having a greater Zone of Inhibition in all cases:
- +2.45 mm for *S. aureus* ATCC 33592 (MRSA)
- +0.37 mm for *E. coli* ATCC BAA-196 (ESBL)
- +2.55 mm for *E. faecalis* ATCC 51575 (VRE)
- +0.36 mm for *P. aeruginosa* ATCC BAA-2114 (Multi-Drug Resistant)
- +0.65 mm for *A. baumannii* ATCC BAA-1605 (Multi-Drug Resistant)

The gel contact member provides a zone of inhibition 14 under and around the electrode 10 having a size that is greater than the size of the electrode 10. The average zone of inhibition 14 may be at least about 0.5 mm to about 6 mm. The average zone of inhibition may range from at least about 0.55 mm to about 5.65 mm. The average zone of inhibition may range from at least about 0.65 mm to about 5.25 mm.

There was no zone of inhibition found for *E. cloacae* ATCC BAA-2468 (CRE). While there was no zone of inhibition around the coupon during testing, the anti-microbial gel killed and deterred grown under the coupon. The zone of inhibition for *S. aureus* ATCC 33592 (MRSA) may range from at least about 4.75 mm to about 5.65 mm, or from about 4 mm to about 6 mm, or from about 4.5 mm to about 5.5 mm. The zone of inhibition for *E. coli* ATCC BAA-196 (ESBL) may range from at least about 1.35 mm to about 2.0 mm, from about 1 mm to about 3 mm, or from about 1 mm to about 2 mm. The zone of inhibition for *E. faecalis* ATCC 51575 (VRE) may range from 2.6 mm to about 4.4 mm, or from about 2 mm to about 5 mm, or from about 3 mm to about 4.5 mm. The zone of inhibition for *P. aeruginosa* ATCC BAA-2114 (Multi-Drug Resistant) may range from about 0.55 mm to about 1.85 mm, or about 0.5 mm to about 2 mm., or from about 0.5 mm to about 1.9 mm. The zone of inhibition for *A. baumannii* ATCC BAA-1605 (Multi-Drug Resistant) may range from about 0.35 mm to about 0.90 mm, or about 0.2 mm to about 1 mm., or from about 0.3 mm to about 1 mm, or from about 0.3 mm to about 0.9 mm.

In conducting the testing, the Anti-microbial gel and control substance Promeon M862 gel, were subjected to simulated use cycles involving 10 contacts for 30 minutes each on human skin. A subject's skin was washed and thoroughly dried. Hands of the sample preparer/handler were also washed and dried prior to initiating and completing each cycle (to simulate typical clinical procedures of handwashing between patients). The preparer removed each test pad from its storage sleeve one at a time and placed the pad on the prepared skin surface of the subject.

These cycles were also conducted with three control coupons that consisted of sterilized, untreated cotton fabric swatches. The controls were applied in the same manner as the test substances. Three cotton swatches were applied on the subject's left forearm and held in place with a first aid elastic bandage. All control samples (Promeon Gel) were placed for on the subject's right-side extremities. All test samples (anti-microbial gel) were placed after all control samples were placed and were placed on the subjects' left side extremities. The samples were left in place for 30 minutes. The subject was instructed to remain seated and to not touch or disturb the samples. The sample handler removed the controls and the test coupons and stored them by placing them on storage cards in storage sleeves or bags.

This process was repeated 10 times (up to 2 times a day for 5 days) for each of the samples. A minimum of 2 hours elapsed between each simulated use on any given day. The samples were only in contact with the subject skin, the hands of the handler, or the associated storage device.

To be aseptically harvested, following final application, the control swatches were placed into 3 conical vials (1 each) containing 20 ml sterile phosphate buffered saline. Test substances were stored at room temperature under fluorescent lighting.

The test and control substances were then aseptically cut into half, with one half being used for the AATCC 100 testing while the other half was used for the Zone of Inhibition testing.

The test and control substances were then cut into approximately 1"×2" coupons. Three of each substance type and the control coupons were enumerated to determine the baseline level of background contamination from the environment that the coupons collected during the simulated use cycles. Those results can be seen in Table 14 above.

The inhibitory properties of the test substances were tested by placing a coupon of the substance on inoculated agar plates and then incubating them for 24±1 hours at 36±1° C. Growth of the test microorganisms was evaluated under each test or control substance coupon as well as around each coupon. The zones observed for each microorganism with both test substance types is shown in Table 7 above. Bot the test and control substances prevented growth of all test microorganisms where each coupon remained in contact with the agar (under each coupon). Photos were taken of the representative zones of inhibition, which are shown in FIGS. 4-9.

The efficacy of the test substances was tested by directly inoculating the coupons and incubating them for 24±1 hours at 36±1° C. The control coupons were also inoculated and incubated under the same conditions. Reductions were calculated based on the initial number controls and parallel controls. The anti-microbial gel demonstrated more than a 4 $\log_{10}$ reduction against all test microorganisms. The exact $\log_{10}$ reductions against each microorganism and for both test substance types is shown in Tables 1-6 above.

Three of each dressing type was harvested to determine the level of baseline contamination from the simulated use cycles.

The following procedure was used for the AATCC 100 portion of the test. The test culture and test inoculum were then prepared. A new test culture of each test microorganism was initiated by transferring a loop of target microorganism to a test tube containing 10 ml sterile tryptic soy broth (TSB). The test culture tubes were incubated for 24±1 hours at 36±1° C. Test cultures containing *P. aeruginosa* were decanted prior to diluting to avoid the pellicle. Test cultures were diluted in simulated wound fluid to yield the appropriate test inoculum concentration targeting approximately $1 \times 10^7$ CFU/ml.

The test inocula was then enumerated. Each diluted test culture was enumerated on a per ml basis so as to determine the concentration of the test inocula. Each test inocula was serially diluted in Phosphate Buffered Saline (PBS) and a range of concentrations was plated to TSA. Standard pour-plating techniques were used to plate the dilutions. Enumeration plates were incubated for 48±6 hours at 36±1° C.

The initial numbers control was then determined (i.e., Time Zero Control). To determine the baseline level of target test organism added to test dressings, triple replicate control dressings were inoculated with 0.5 ml of the prepared test inoculum using spot inoculation techniques. Immediately following inoculation, each dressing was aseptically harvested in 20 ml D/E neutralization broth. Harvested dressings were then vortex-mixed for 60±5 seconds. The resulting tubes were enumerated using standard serial dilution and enumeration techniques to establish a time zero count. The initial numbers control was performed in triple replicate for each microorganism.

The test and control substances were then inoculated. The test and control dressings were aseptically placed in sterile petri dishes. All test and control dressings were inoculated with 0.5 ml of test inoculum using spot inoculation techniques. After inoculation, petri dishes were lidded and placed in a resealable bag with a moistened paper towel. The dressings were allowed to incubate for 24±1 hour at 36±1° C. At the end of each contact time, test and control dressings were aseptically harvested in 20 ml D/E neutralization broth. Harvested dressings were then vortex-mixed for 60±5 seconds. The resulting tubes were enumerated using standard serial dilution and enumeration techniques toe stablish the concentration of surviving microorganisms.

Neutralization was then verified for each microorganism for each hydrogel type. One anti-microbial hydrogel test dressing and one Promeon dressing were harvested in 20 ml D/E neutralization broth and vortex mixed for 60±5 seconds to create neutralization test suspensions. Separately, a control dressing was harvested in a similar manner to create a control neutralization suspension. Individual test microorganisms were diluted in phosphate buffered sale (PBS) to create a neutralization inoculum with a target concentration of 5-100 CFU per 0.100 ml of inoculum. The two neutralization test suspensions and one neutralization control suspension were batched out in 0.900 ml aliquots in sterile microcentrifuge tubes. Each 0.900 ml suspension was inoculated with 0.100 ml of neutralization inoculum, which was prepared as described above. The neutralization test and control suspensions were sufficiently vortexed before being allowed to sit for a hold period of ≥10 minutes. Then each microcentrifuge tube was plated entirely (about 1 ml each), pour plating with TSA. Neutralization of the active ingredient was considered valid if ≥70% of the microorganisms in the neutralization test suspension were recovered compared to the respective microorganism concentration of the neutralization control suspension. The neutralization control must have a CFU count of 5-100 microorganisms.

The following procedure was used for Zone of Inhibition testing. The test culture and test inoculum were prepared. A new test culture of each test microorganism was initiated by a loop of target microorganism (from the most recent working stock or daily subculture) to a test tube containing 10 ml sterile tryptic soy broth. Test culture tubes were incubated at 36±1° C. for 24±4 hours. Test cultures containing *P. aeruginosa* were decanted prior to diluting to avoid the pellicle. The test culture was diluted in phosphate buffered saline, if necessary, to yield the appropriate test inoculum concentration targeting approximately $1 \times 10^8$ CFU/ml.

The inoculated swabs were then enumerated. A sterile swab was placed into a tube of prepared test inoculum and used to inoculate three solidified agar plates. The swab was not re-dipped in the inoculum in between inoculating each plate. The same swab was then aseptically cut or broken into a 50 ml conical vial containing 10 ml of sterile PBS. The harvested swab was vortex mixed for 30±5 seconds and serially diluted and plated in a petri dish 46 using standard enumeration techniques. The previous three steps were repeated for each test microorganism such that one swab was enumerated for each microorganism species.

The test plates were then prepared and inoculated. Tryptic soy agar was poured into sterile petri dishes and allowed to solidify prior to inoculating the surface of each plate. Each test place was swab inoculated with one test microorganism for by dipping a sterile swab into the prepared test inoculum and streaking the surface of the agar three times, turning the plate at a 120° angle each time, until the entire surface was inoculated. The same swab was not re-dipped in inoculum and was used to inoculate two more plates.

The test substance was then added to the test plates 46. The shorter width of the test coupon was measured using digital calipers prior to adding to the agar. Films and plastics were removed prior to placing the hydrogel on the inoculated agar. The side not touching the agar may still have a film on it. The test substances were added to the middle of each inoculated test plate. One test coupon was used per plate. A sterile stainless-steel carrier was added to the top of each hydrogel coupon to minimize curling during the contact time. Test plates 46 were allowed to incubate for 24±1 hour at 36±1° C.

The zones of inhibition were then recorded using digital calipers after the contact time was observed. Zones were measured from the edge of the square coupon to the beginning of microbial growth. Growth of each test microorganism was assessed under the test coupons as well as around the coupons. Representative photos are shown in FIGS. 4-9.

A 4 $\log_{10}$ was demonstrated, showing that the topical skin dressing was considered efficacious against the microorganisms. The anti-microbial gel demonstrated more than a 4 $\log_{10}$ reduction against all test microorganisms. The exact $\log_{10}$ reductions against each microorganism and for both test substance types can be observed in tables 1, 2, 3, 4, 5 and 6.

Figure 4:
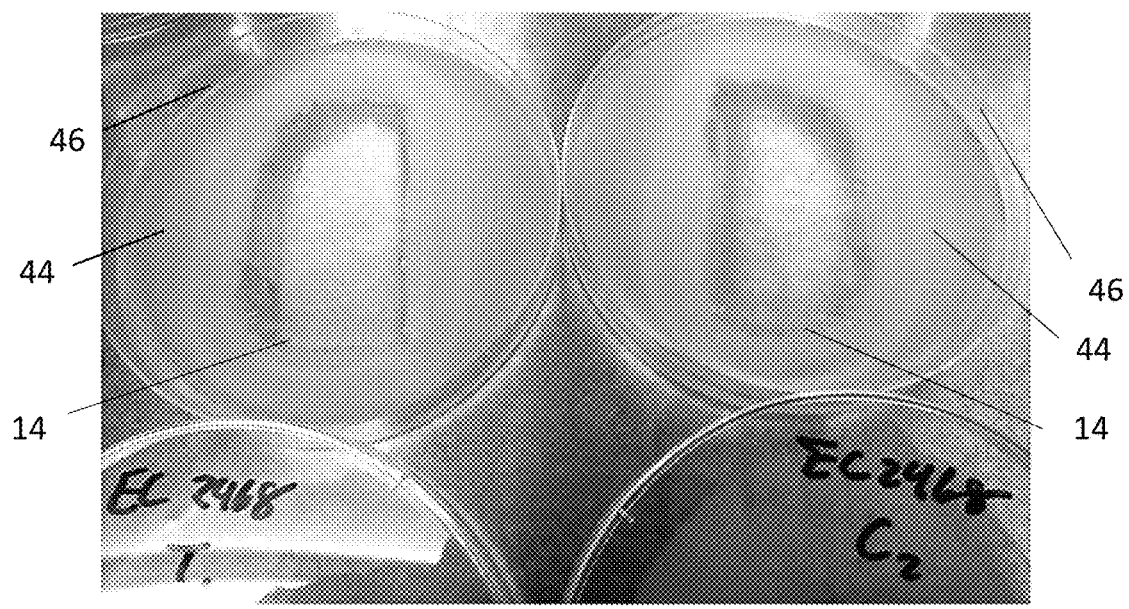
FIG. 4 depicts testing samples after removal of a test/control substances.
Figure 5:
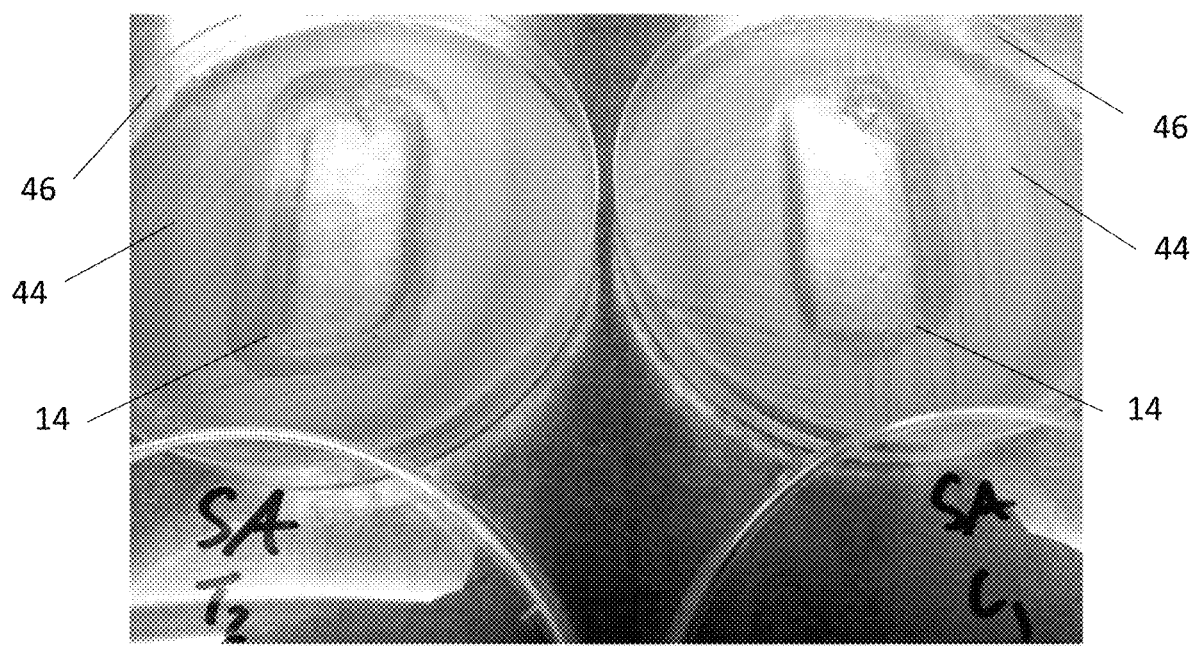
FIG. 5 depicts testing samples after removal of a test/control substances.
Figure 6:
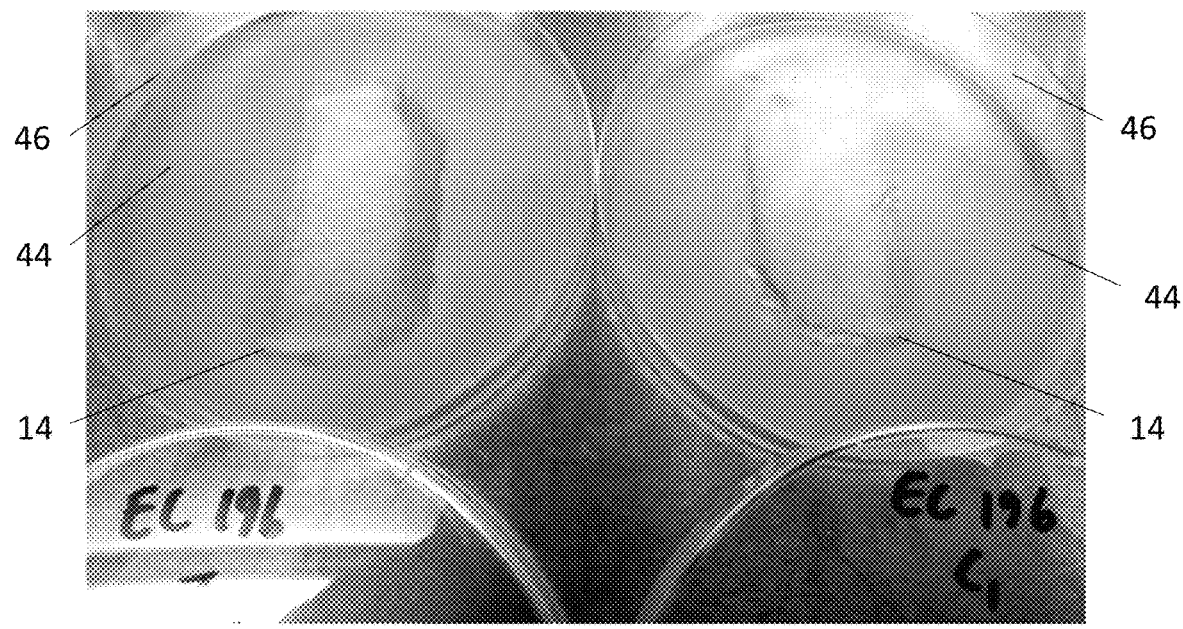
FIG. 6 depicts testing samples after removal of a test/control substances.
Figure 7:
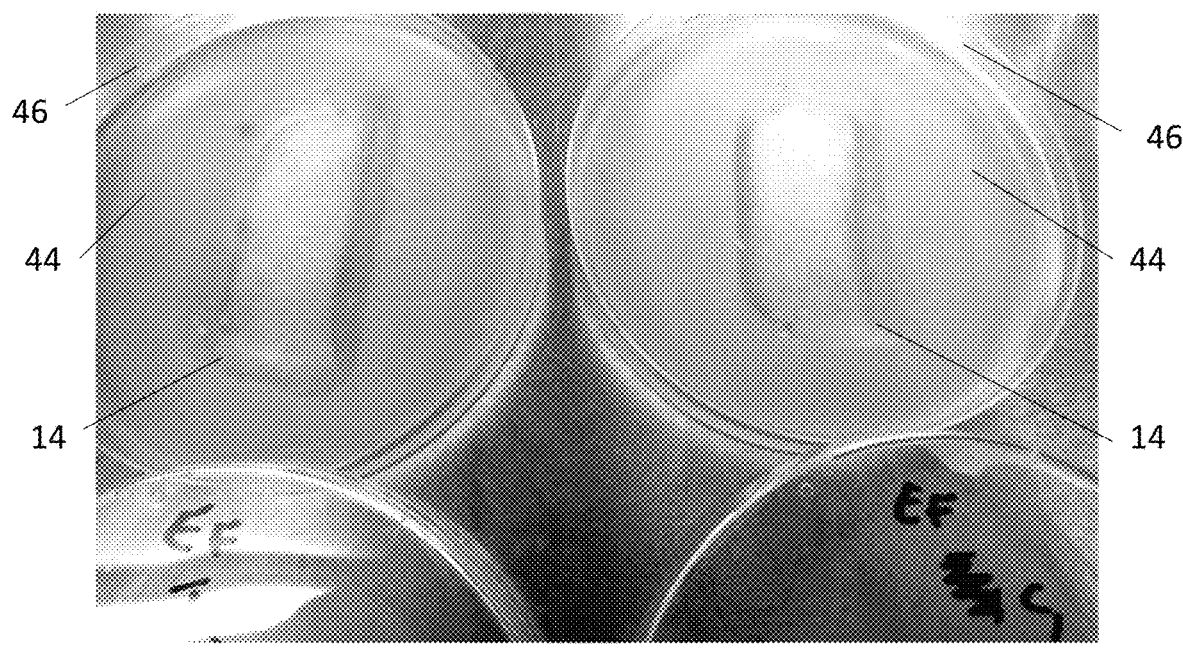
FIG. 7 depicts testing samples after removal of a test/control substances.
Figure 8:
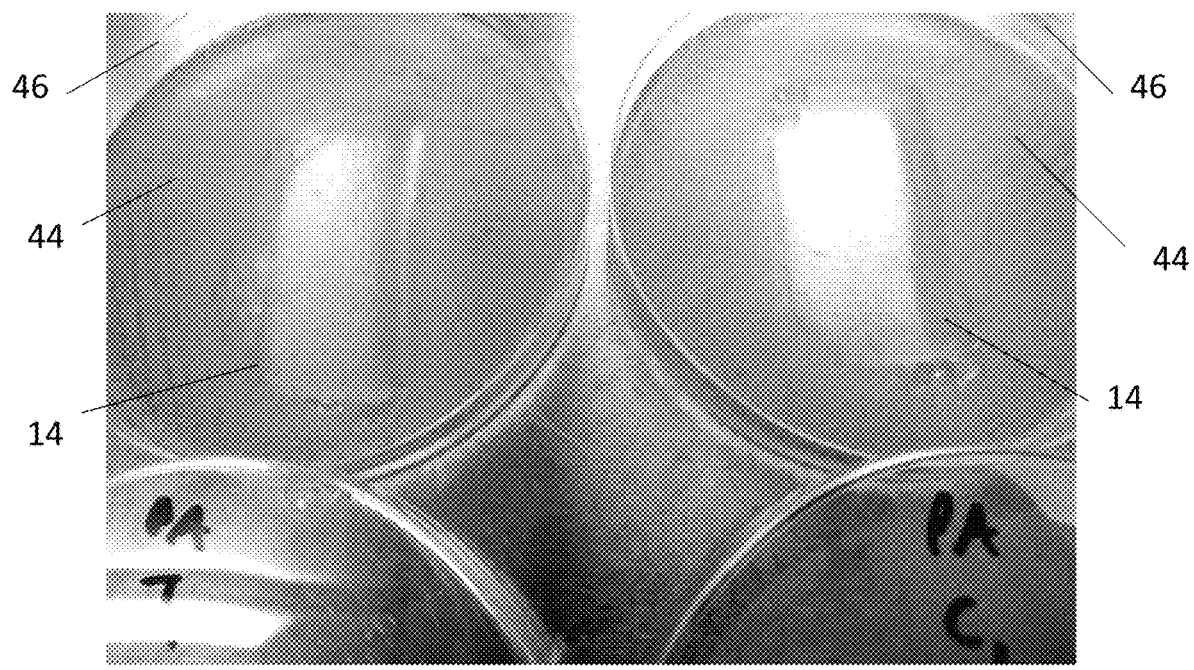
FIG. 8 depicts testing samples after removal of a test/control substances.
Figure 9:
FIG. 9 depicts testing samples after removal of a test/control substances.

Referring to the Figures, FIGS. 4-9 depict test results in a petri dish 46. FIG. 4 depicts a photograph of *E. cloacae* ATCC BAA-2468 (CRE) replicates with anti-microbial gel on the left side and Promeon M862 gel on the right side after removal of test/control substances. FIG. 5 depicts a photograph of *S. aureus* ATCC 33592 (MRSA) replicates with anti-microbial gel on the left side and Promeon M862 gel on the right side after removal of test/control substances. FIG. 6 depicts a photograph of *E. coli* ATCC BAA-196 (ESBL) replicates with anti-microbial gel on the left side and Promeon M862 gel on the right side after removal of test/control substances. FIG. 7 depicts a photograph of *E. faecalis* ATCC 51575 (VRE) replicates with anti-microbial gel on the left side and Promeon M862 gel on the right side after removal of test/control substances. FIG. 8 depicts a photograph of *P. aeruginosa* ATCC BAA-2114 (Multi-drug resistant) replicates with anti-microbial gel on the left side and Promeon M862 gel on the right side after removal of test control substances. FIG. 9 depicts a photograph of *A. baumannii* ATCC BAA-1605 (Multi-drug resistant) replicates with anti-microbial gel on the left side and Promeon M862 gel on the right side after removal of test/control substances.

According to one embodiment, a biomedical electrode for electrically contacting a user's skin includes a carrier layer, a backing layer, an electrical lead, a conductive member, and a gel contact member. The backing layer is disposed on the carrier layer. The electrical lead is positioned at least in part below the carrier layer. The conductive member is coupled to the electrical lead. The gel contact member is electrically coupled to the conductive member for directly contacting the user's skin. The gel contact member is electrically conductive. The gel contact member includes a gel combined with an anti-microbial agent.

The gel contact member may inhibit the growth of microbes, prevent the growth of microbes, or kill microbes under the gel contact member. The gel contact member may provide a zone of inhibition around the electrode having a size that is greater than the size of the electrode. The zone of inhibition is a zone where microbes are killed, where growth of microbes is inhibited, where growth of microbes is prevented, or a combination thereof. The zone of inhibition may be at least about 0.5 mm.

The electrical lead may be a lead wire that extends through the carrier layer and has a connector at one end for attaching to an external device. The electrical lead may be coupled to the conductive member at the other end for providing an electrical current to the conductive member. The gel may be an acrylic hydrogel and the anti-microbial agent may be a quaternary ammonium salt. The anti-microbial agent may be BEC. The BEC may be 0.2% BEC.

The carrier layer may be a cloth, foam, or vinyl layer, or a combination thereof. The carrier layer may include a removable backing layer coupled to the gel contact member. The conductive member may be made at least in part of a conductive material. The conductive member may be a carbon-filled polymeric film.

The gel contact member may have adhesive properties for coupling to a user's skin in the range of about 185 grams/in to about 240 grams/in. The anti-microbial agent may have one or more of bacteriostatic or bactericidal properties.

In another embodiment, a gel contact member for an electrode includes, in combination, a gel material mixed with an anti-microbial material. The combination is applied to a surface of an electrode for adhering to the skin of a user. The gel contact member inhibits the growth of microbes at least one of under and around the gel contact member and has one or more of bacteriostatic or bactericidal properties.

The gel material may be an acrylic hydrogel and the anti-microbial material may be quaternary ammonium chloride. The gel material may be BEC. The gel material may be 0.2% BEC.

The gel contact member may have adhesive properties that permit the gel contact member to attach to a user's skin, be retained on a user's skin, and be removable from a user's skin. The gel contact member, when applied to a user's skin, affects microbes under the electrode, including or selected from a group consisting of: *E. cloacae* ATCC BAA-2468 (CRE), *S. aureus* ATCC 33592 (MRSA), *E. coli* ATCC BAA-196 (ESBL), *E. faecalis* ATCC 51575 (VRE), *A. baumannii* ATCC BAA-1605 (Multi-Drug Resistant). The microbes that are affected in a zone of inhibition around the electrode include or are selected from a group consisting of: *S. aureus* ATCC 33592 (MRSA), *E. coli* ATCC BAA-196 (ESBL), *E. faecalis* ATCC 51575 (VRE), *P. aeruginosa* ATCC BAA-2114 (Multi-Drug Resistant), and *A. baumannii* ATCC BAA-1605 (Multi-Drug Resistant).

In another embodiment, a method of killing, inhibiting growth, or preventing growth of microbes that cause infectious disease in a mammal utilizing the electrode described above including installing the electrode on the skin of a user. The microbes that are affected under the electrode include or are selected from the group consisting of: *E. cloacae* ATCC BAA-2468 (CRE), *S. aureus* ATCC 33592 (MRSA), *E. coli* ATCC BAA-196 (ESBL), *E. faecalis* ATCC 51575 (VRE), *P. aeruginosa* ATCC BAA-2114 (Multi-Drug Resistant), and *A. baumannii* ATCC BAA-1605 (Multi-Drug Resistant). The microbes that are affected in a zone of inhibition around the electrode include or are selected from the group consisting of: *S. aureus* ATCC 33592 (MRSA), *E. coli* ATCC BAA-196 (ESBL), *E. faecalis* ATCC 51575 (VRE), *P. aeruginosa* ATCC BAA-2114 (Multi-Drug Resistant), and *A. baumannii* ATCC BAA-1605 (Multi-Drug Resistant).

The zone of inhibition associated with each microbe may range from about 4.75 mm to about 5.65 mm for *S. aureus* ATCC 33592 (MRSA), from about 1.35 mm to about 2.0 mm for *E. coli* ATCC BAA-196 (ESBL), from about 2.6 mm to about 4.4 mm for *E. faecalis* ATCC 51575 (VRE), from about 0.55 mm to about 1.85 mm for *P. aeruginosa* ATCC BAA-2114 (Multi-Drug Resistant), and from about 0.35 mm to about 0.90 mm for *A. baumannii* ATCC BAA-1605 (Multi-Drug Resistant).

Various brand names for BEC containing products presently on the market include Salanine™, BZT™, Diapp™, Quatrachlor™, Polymine D™, Phemithyn™, Antiseptor™, Disilyn™, Phermerol™ and others. Any of these brands could be used as the anti-microbial component discussed herein.

The term "substantially," if used herein, is a term of estimation.

While various features are presented above, it should be understood that the features may be used singly or in any combination thereof. Further, it should be understood that variations and modifications may occur to those skilled in the art to which the claimed examples pertain. The examples described herein are exemplary. The disclosure may enable those skilled in the art to make and use alternative designs having alternative elements that likewise correspond to the elements recited in the claims. The intended scope may thus include other examples that do not differ or that insubstantially differ from the literal language of the claims. The scope of the disclosure is accordingly defined as set forth in the appended claims.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim. The term "consisting essentially," if used herein, means the specified materials or steps and those that do not materially affect the basic and novel characteristics of the material or method. All percentages and averages are by weight unless the context indicates otherwise. If not specified above, the properties mentioned herein may be determined by applicable ASTM standards, or if an ASTM standard does not exist for the property, the most commonly used standard known by those of skill in the art may be used. The articles "a," "an," and "the," should be interpreted to mean "one or more" unless the context indicates the contrary.

What is claimed is:

1. A method of killing, inhibiting growth, or preventing growth of microbes that cause infectious disease in a mammal utilizing an electrode comprising a reusable biomedical electrode for electrically contacting a user's skin having:
   a carrier layer;
   a backing layer disposed on the carrier layer;
   an electrical lead positioned at least in part below the carrier layer;
   a conductive member coupled to the electrical lead; and
   a gel contact member coupled to the conductive member for directly contacting the user's skin, said gel contact member being electrically conductive, wherein the gel contact member includes a gel combined with an anti-microbial agent,
   wherein the gel contact member inhibits the growth of microbes, prevents growth of microbes, or kills microbes under the gel contact member, and
   wherein the gel contact member provides a zone of inhibition around the electrode having a size that is greater than the size of the electrode, with the zone of inhibition being a zone where microbes are killed, where growth of microbes is prevented, or a combination thereof,
   the method comprising:
   installing the electrode on the skin of a user, wherein the microbes that are affected under the electrode are selected from the group consisting of:
      E. cloacae ATCC BAA-2468 (CRE),
      S. aureus ATCC 33592 (MRSA),
      E. coli ATCC BAA-196 (ESBL),
      E. faecalis ATCC 51575 (VRE),
      P. aeruginosa ATCC BAA-2114 (Multi-Drug Resistant), and
      A. baumannii ATCC BAA-1605 (Multi-Drug Resistant);
   the microbes that are affected in a zone of inhibition around the electrode are selected from the group consisting of:
      S. aureus ATCC 33592 (MRSA),
      E. coli ATCC BAA-196 (ESBL),
      E. faecalis ATCC 51575 (VRE),
      P. aeruginosa ATCC BAA-2114 (Multi-Drug Resistant), and
      A. baumannii ATCC BAA-1605 (Multi-Drug Resistant);
   wherein the zone of inhibition associated with each microbe ranges from about 4.75 mm to about 5.65 mm for S. aureus ATCC 33592 (MRSA), from about 1.35 mm to about 2.0 mm for E. coli ATCC BAA-196 (ESBL), from about 2.6 mm to about 4.4 mm for E. faecalis ATCC 51575 (VRE), from about 0.55 mm to about 1.85 mm for P. aeruginosa ATCC BAA-2114 (Multi-Drug Resistant), and from about 0.35 mm to about 0.90 mm for A. baumannii ATCC BAA-1605 (Multi-Drug Resistant).

2. A method of killing, inhibiting growth, or preventing growth of microbes that cause infectious disease in a mammal utilizing a reusable biomedical electrode for electrically contacting a user's skin comprising:
   a carrier layer;
   a backing layer disposed on the carrier layer;
   an electrical lead positioned at least in part below the carrier layer;
   a conductive member coupled to the electrical lead; and
   a gel contact member electrically coupled to the conductive member for directly contacting the user's skin, said gel contact member being electrically conductive, wherein the gel contact member includes a gel mixed with an anti-microbial agent, wherein the gel contact member inhibits growth of microbes at least one of under and around the gel contact member and has one or more of bacteriostatic and bactericidal properties to prevent the gel contact member from being contaminated so that it may be used multiple times, wherein the gel contact member, prevents growth of microbes, or kills microbes under the gel contact member and within the gel contact member to permit multiple uses of the electrode, and wherein the gel contact member provides a zone of inhibition around the electrode on a user's skin having a size that is greater than the size of the electrode, with the zone of inhibition on user's skin being a zone where microbes are killed, where growth of microbes is inhibited, where growth of microbes is prevented, or a combination thereof;
   the method comprising:
   installing the electrode on the skin of a user, wherein the microbes that are affected under the electrode are selected from the group consisting of:
      E. cloacae ATCC BAA-2468 (CRE),
      S. aureus ATCC 33592 (MRSA),
      E. coli ATCC BAA-196 (ESBL),
      E. faecalis ATCC 51575 (VRE),
      P. aeruginosa ATCC BAA-2114 (Multi-Drug Resistant), and
      A. baumannii ATCC BAA-1605 (Multi-Drug Resistant); and
   the microbes that are affected in a zone of inhibition around the electrode are selected from the group consisting of:
      S. aureus ATCC 33592 (MRSA),
      E. coli ATCC BAA-196 (ESBL),
      E. faecalis ATCC 51575 (VRE),
      P. aeruginosa ATCC BAA-2114 (Multi-Drug Resistant), and
      A. baumannii ATCC BAA-1605 (Multi-Drug Resistant),
   wherein the zone of inhibition associated with S. aureus ATCC 33592 (MRSA) ranges from about 4.75 mm to about 5.65 mm.

3. A method of killing, inhibiting growth, or preventing growth of microbes that cause infectious disease in a mammal utilizing a reusable biomedical electrode for electrically contacting a user's skin comprising:
- a carrier layer;
- a backing layer disposed on the carrier layer;
- an electrical lead positioned at least in part below the carrier layer;
- a conductive member coupled to the electrical lead; and
- a gel contact member electrically coupled to the conductive member for directly contacting the user's skin, said gel contact member being electrically conductive, wherein the gel contact member includes a gel mixed with an anti-microbial agent, wherein the gel contact member inhibits growth of microbes at least one of under and around the gel contact member and has one or more of bacteriostatic and bactericidal properties to prevent the gel contact member from being contaminated so that it may be used multiple times, wherein the gel contact member, prevents growth of microbes, or kills microbes under the gel contact member and within the gel contact member to permit multiple uses of the electrode, and wherein the gel contact member provides a zone of inhibition around the electrode on a user's skin having a size that is greater than the size of the electrode, with the zone of inhibition on the user's skin being a zone where microbes are killed, where growth of microbes is inhibited, where growth of microbes is prevented, or a combination thereof;

the method comprising:
installing the electrode on the skin of a user, wherein the microbes that are affected under the electrode are selected from the group consisting of:
- E. cloacae ATCC BAA-2468 (CRE),
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant); and the microbes that are affected in a zone of inhibition around the electrode are selected from the group consisting of:
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant), wherein the zone of inhibition associated with E. coli ATCC BAA-196 (ESBL) ranges from about 1.35 mm to about 2.0 mm.

4. A method of killing, inhibiting growth, or preventing growth of microbes that cause infectious disease in a mammal utilizing a reusable biomedical electrode for electrically contacting a user's skin comprising:
- a carrier layer;
- a backing layer disposed on the carrier layer;
- an electrical lead positioned at least in part below the carrier layer;
- a conductive member coupled to the electrical lead; and
- a gel contact member electrically coupled to the conductive member for directly contacting the user's skin, said gel contact member being electrically conductive, wherein the gel contact member includes a gel mixed with an anti-microbial agent, wherein the gel contact member inhibits growth of microbes at least one of under and around the gel contact member and has one or more of bacteriostatic and bactericidal properties to prevent the gel contact member from being contaminated so that it may be used multiple times, wherein the gel contact member, prevents growth of microbes, or kills microbes under the gel contact member and within the gel contact member to permit multiple uses of the electrode, and wherein the gel contact member provides a zone of inhibition around the electrode on a user's skin having a size that is greater than the size of the electrode, with the zone of inhibition on the user's skin being a zone where microbes are killed, where growth of microbes is inhibited, where growth of microbes is prevented, or a combination thereof;

the method comprising:
installing the electrode on the skin of a user, wherein the microbes that are affected under the electrode are selected from the group consisting of:
- E. cloacae ATCC BAA-2468 (CRE),
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant); and the microbes that are affected in a zone of inhibition around the electrode are selected from the group consisting of:
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant), wherein the zone of inhibition associated with E. faecalis ATCC 51575 (VRE) ranges from about 2.6 mm to about 4.4 mm.

5. A method of killing, inhibiting growth, or preventing growth of microbes that cause infectious disease in a mammal utilizing a reusable biomedical electrode for electrically contacting a user's skin comprising:
- a carrier layer;
- a backing layer disposed on the carrier layer;
- an electrical lead positioned at least in part below the carrier layer;
- a conductive member coupled to the electrical lead; and
- a gel contact member electrically coupled to the conductive member for directly contacting the user's skin, said gel contact member being electrically conductive, wherein the gel contact member includes a gel mixed with an anti-microbial agent, wherein the gel contact member inhibits growth of microbes at least one of under and around the gel contact member and has one or more of bacteriostatic and bactericidal properties to prevent the gel contact member from being contaminated so that it may be used multiple times, wherein the gel contact member, prevents growth of microbes, or kills microbes under the gel contact member and within the gel contact member to permit multiple uses of the electrode, and wherein the gel contact member provides a zone of inhibition around the electrode on a user's skin having a size that is greater than the size of the electrode, with the zone of inhibition on the user's skin being a zone where microbes are killed, where growth of microbes is inhibited, where growth of microbes is prevented, or a combination thereof;

the method comprising:

installing the electrode on the skin of a user, wherein the microbes that are affected under the electrode are selected from the group consisting of:
- E. cloacae ATCC BAA-2468 (CRE),
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant); and the microbes that are affected in a zone of inhibition around the electrode are selected from the group consisting of:
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant), wherein the zone of inhibition associated with P. aeruginosa ATCC BAA-2114 (Multi-Drug Resistant) ranges from about 0.55 mm to about 1.85 mm.

6. A method of killing, inhibiting growth, or preventing growth of microbes that cause infectious disease in a mammal utilizing a reusable biomedical electrode for electrically contacting a user's skin comprising:

a carrier layer;

a backing layer disposed on the carrier layer;

an electrical lead positioned at least in part below the carrier layer;

a conductive member coupled to the electrical lead; and a gel contact member electrically coupled to the conductive member for directly contacting the user's skin, said gel contact member being electrically conductive, wherein the gel contact member includes a gel mixed with an anti-microbial agent, wherein the gel contact member inhibits growth of microbes at least one of under and around the gel contact member and has one or more of bacteriostatic and bactericidal properties to prevent the gel contact member from being contaminated so that it may be used multiple times, wherein the gel contact member, prevents growth of microbes, or kills microbes under the gel contact member and within the gel contact member to permit multiple uses of the electrode, and wherein the gel contact member provides a zone of inhibition around the electrode on a user's skin having a size that is greater than the size of the electrode, with the zone of inhibition on the user's skin being a zone where microbes are killed, where growth of microbes is inhibited, where growth of microbes is prevented, or a combination thereof;

the method comprising:

installing the electrode on the skin of a user, wherein the microbes that are affected under the electrode are selected from the group consisting of:
- E. cloacae ATCC BAA-2468 (CRE),
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant); and the microbes that are affected in a zone of inhibition around the electrode are selected from the group consisting of:
- S. aureus ATCC 33592 (MRSA),
- E. coli ATCC BAA-196 (ESBL),
- E. faecalis ATCC 51575 (VRE),
- P. aeruginosa ATCC BAA-2114 (Multi-Drug Resistant), and
- A. baumannii ATCC BAA-1605 (Multi-Drug Resistant), wherein the zone of inhibition associated with A. baumannii ATCC BAA-1605 (Multi-Drug Resistant) ranges from about 0.35 mm to about 0.90 mm.

* * * * *